US010618892B2

(12) United States Patent
Morris et al.

(10) Patent No.: US 10,618,892 B2
(45) Date of Patent: Apr. 14, 2020

(54) PROCESSES FOR THE PREPARATION OF A BACE INHIBITOR

(71) Applicant: Merck Sharp & Dohme Corp., Rahway, NJ (US)

(72) Inventors: William J. Morris, Springfield, NJ (US); David Thaisrivongs, Cranford, NJ (US); Thomas W. Lyons, Brookline, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 57 days.

(21) Appl. No.: 15/998,903

(22) PCT Filed: Feb. 10, 2017

(86) PCT No.: PCT/US2017/017364
§ 371 (c)(1),
(2) Date: Aug. 16, 2018

(87) PCT Pub. No.: WO2017/142804
PCT Pub. Date: Aug. 24, 2017

(65) Prior Publication Data
US 2020/0039975 A1 Feb. 6, 2020

Related U.S. Application Data

(60) Provisional application No. 62/296,358, filed on Feb. 17, 2016.

(51) Int. Cl.
*C07D 417/12* (2006.01)
(52) U.S. Cl.
CPC .................. *C07D 417/12* (2013.01)
(58) Field of Classification Search
CPC .................................. C07D 417/12
See application file for complete search history.

(56) References Cited

U.S. PATENT DOCUMENTS

| 3,627,771 | A | 12/1971 | Kwok et al. | |
| 8,729,071 | B2 * | 5/2014 | Scott | C07D 403/12 |
| | | | | 514/222.5 |
| 8,940,748 | B2 | 1/2015 | Scott et al. | |
| 9,029,362 | B2 | 5/2015 | Scott et al. | |
| 9,428,475 | B2 | 8/2016 | Scott et al. | |
| 9,447,085 | B2 * | 9/2016 | Cumming | C07D 417/12 |
| 9,475,785 | B2 | 10/2016 | Scott et al. | |
| 10,064,869 | B2 * | 9/2018 | Scobie | A61K 31/506 |
| 10,329,291 | B2 * | 6/2019 | Scott | C07D 417/12 |
| 2012/0183563 | A1 * | 7/2012 | Scott | C07D 487/04 |
| | | | | 424/172.1 |
| 2014/0023668 | A1 | 1/2014 | Cumming et al. | |
| 2016/0016921 | A1 | 1/2016 | Khan et al. | |
| 2016/0016923 | A1 * | 1/2016 | Khan | C07D 419/12 |
| | | | | 514/222.5 |
| 2016/0222032 | A1 * | 8/2016 | Scott | A61K 31/547 |
| 2016/0326155 | A1 * | 11/2016 | Scott | C07D 417/12 |
| 2016/0367563 | A1 | 12/2016 | Scott et al. | |
| 2017/0233382 | A1 * | 8/2017 | Miller | C07C 311/35 |
| | | | | 544/8 |
| 2017/0246300 | A1 * | 8/2017 | He | C07D 417/12 |
| 2017/0260181 | A1 * | 9/2017 | Cumming | C07D 471/04 |
| 2017/0369484 | A1 * | 12/2017 | Wu | C07D 417/12 |

FOREIGN PATENT DOCUMENTS

| WO | WO-2011044181 A1 * | 4/2011 | ............ A61K 31/00 |
| WO | WO-2014099768 A1 * | 6/2014 | |
| WO | 2016025359 A1 | 2/2016 | |
| WO | WO-2016053767 A1 * | 4/2016 | ........... C07D 417/12 |

OTHER PUBLICATIONS

M. Zajac et al., 15 Chemistry A European Journal, 8204-8222 (2009) (Year: 2009).*
L. Artino et al., 22 Organic Process Research & Development, 385-390 (2018) (Year: 2018).*
D.A. Thaisrivongs et al., 20 Organic Letters, 1568-1571 (2018) (Year: 2018).*
International Search Report for PCT/US2017/017364 dated Apr. 14, 2017, 9 pages.

* cited by examiner

*Primary Examiner* — Alexander R Pagano
(74) *Attorney, Agent, or Firm* — Keith D. MacMillan; Catherine D. Fitch

(57) ABSTRACT

This invention provides an improved processes for the preparation of verubecestat (Compound of Formula (I)), a potent inhibitor of BACE-1 and BACE-2.

9 Claims, No Drawings

PROCESSES FOR THE PREPARATION OF A BACE INHIBITOR

FIELD OF THE INVENTION

This invention provides an improved processes for the preparation of verubecestat (Compound of Formula (I)), a potent inhibitor of BACE-1 and BACE-2.

BACKGROUND

Amyloid beta peptide ("Aβ") is a primary component of β amyloid fibrils and plaques, which are regarded as having a role in an increasing number of pathologies. Examples of such pathologies include, but are not limited to, Alzheimer's disease, Down's syndrome, Parkinson's disease, memory loss (including memory loss associated with Alzheimer's disease and Parkinson's disease), attention deficit symptoms (including attention deficit symptoms associated with Alzheimer's disease ("AD"), Parkinson's disease, and Down's syndrome), dementia (including pre-senile dementia, senile dementia, dementia associated with Alzheimer's disease, Parkinson's disease, and Down's syndrome), progressive supranuclear palsy, cortical basal degeneration, neurodegeneration, olfactory impairment (including olfactory impairment associated with Alzheimer's disease, Parkinson's disease, and Down's syndrome), β-amyloid angiopathy (including cerebral amyloid angiopathy), hereditary cerebral hemorrhage, mild cognitive impairment ("MCI"), glaucoma, amyloidosis, type II diabetes, hemodialysis (β2 microglobulins and complications arising therefrom), neurodegenerative diseases such as scrapie, bovine spongiform encephalitis, Creutzfeld-Jakob disease, traumatic brain injury and the like. The inhibition of BACE-1 has been shown to inhibit the production of Aβ.

BACE-1 has become an accepted therapeutic target for the treatment of Alzheimer's disease. For example, McConlogue et al., J. Bio. Chem., Vol. 282, No. 36 (September 2007), have shown that partial reductions of BACE-1 enzyme activity and concomitant reductions of Aβ levels lead to a dramatic inhibition of Aβ-driven AD-like pathology, making β-secretase a target for therapeutic intervention in A D. Ohno et al. Neurobiology of Disease, No. 26 (2007), 134-145, report that genetic deletion of BACE-1 in 5XFAD mice abrogates Aβ generation, blocks amyloid deposition, prevents neuron loss found in the cerebral cortex and subiculum (brain regions manifesting the most severe amyloidosis in 5XFAD mice), and rescues memory deficits in 5XFAD mice. The group also reports that Aβ is ultimately responsible for neuron death in AD and concludes that BACE-1 inhibition has been validated as an approach for the treatment of A D. Roberds et al., Human Mol. Genetics, 2001, Vol. 10, No. 12, 1317-1324, established that inhibition or loss of β-secretase activity produces no profound phenotypic defects while inducing a concomitant reduction in Aβ. Luo et al., Nature Neuroscience, Vol. 4, No. 3, March 2001, report that mice deficient in BACE-1 have normal phenotype and abolished β-amyloid generation. More recently, Jonsson, et al. have reported in Nature, Vol. 488, pp. 96-99 (August 2012), that a coding mutation (A673T) in aPP gene protects against Alzheimer's disease and cognitive decline in the elderly without Alzheimer's disease. More specifically, a allele of rs63750847, a single nucleotide polymorphism (SNP), results in an alanine to threonine substitution at position 673 in APP (A673T). This SNP was found to be significantly more common in a healthy elderly control group than in an Alzheimer's disease group. A673T substitution is adjacent to aspartyl protease beta-site in APP, and results in an approximately 40% reduction in the formation of amyloidogenic peptides in a heterologous cell expression system in vitro. Jonsson, et al. report that an APP-derived peptide substrate containing a673T mutation is processed 50% less efficiently by purified human BACE-1 enzyme when compared to a wild-type peptide. Jonsson et al. indicate that the strong protective effect of aPP-A673T substitution against Alzheimer's disease provides proof of principle for the hypothesis that reducing the beta-cleavage of APP may protect against the disease.

The compound:

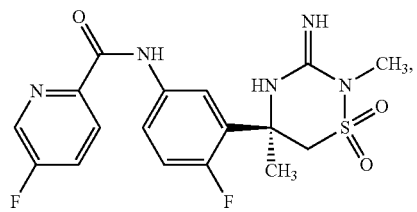 [SMILES: CN1C(=N)N[C@](C)(c2cc(NC(=O)c3ccc(F)cn3)ccc2F)CS1(=O)=O]

and its tautomer:

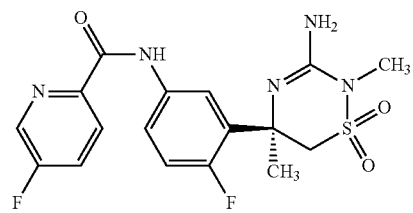 [SMILES: CN1C(N)=N[C@](C)(c2cc(NC(=O)c3ccc(F)cn3)ccc2F)CS1(=O)=O]

which are collectively and individually referred to herein as "verubecestat", or, alternatively, as the "Compound of the Formula (I)", and pharmaceutically acceptable salts thereof, are disclosed in U.S. Pat. No. 8,729,071, PCT Patent Publication No. WO2011/044181, and elsewhere as an inhibitor of BACE-1 and BACE-2, together with pharmaceutical compositions thereof, for use in treating, preventing, ameliorating, and/or delaying the onset of an Aβ pathology, including Alzheimer's disease and mild cognitive impairment, and/or a symptom or symptoms thereof. A preparation of the Compound of Formula (I) is also disclosed therein.

The "endo" (or "amine") tautomer of the Compound of Formula (I), which is shown above, may be depicted as

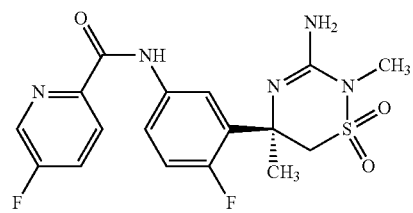 [SMILES: CN1C(N)=N[C@](C)(c2cc(NC(=O)c3ccc(F)cn3)ccc2F)CS1(=O)=O]

and named in the CAS style as N-[3-[(5R)-3-amino-5,6-dihydro-2,5-dimethyl-1,1-dioxido-2H-1,2,4-thiadiazin-5-yl]-4-fluorophenyl]-5-fluoro-2-pyridinecarboxamide, and in the IUPAC style as N-{3-[(5R)-3-amino-2,5-dimethyl-1,1-dioxo-5,6-dihydro-2H-1λ$^6$,2,4-thiadiazin-5-yl]-4-fluorophenyl}-5-fluoropyridine-2-carboxamide.

The "exo" (or "imine") tautomer of the Compound of Formula (I), which is also shown above, may be depicted as

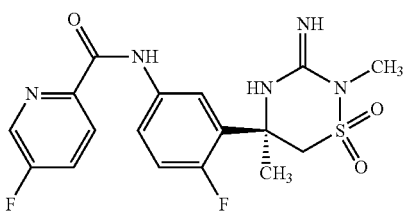 [SMILES: CN1C(=N)N[C@](C)(c2cc(NC(=O)c3ccc(F)cn3)ccc2F)CS1(=O)=O]

and named in the CAS style as 5-fluoro-N-[4-fluoro-3-[(5R)-tetrahydro-3-imino-2,5-dimethyl-1,1-dioxido-2H-1,2,4-thiadiazin-5-yl]phenyl]-2-pyridinecarboxamide, and in the IUPAC style as 5-Fluoro-N-{4-fluoro-3-[(5R)-3-imino-2,5-dimethyl-1,1-dioxo-1$\lambda^6$,2,4-thiadiazinan-5-yl]phenyl}pyridine-2-carboxamide.

U.S. Pat. No. 8,729,071 discloses preparation of the Compound of Formula (I) as Example 25 in Table V through coupling of an appropriate aryl amine and carboxylic acid. While the procedures disclosed therein are suitable for preparing working quantities of the Compound of Formula (I), alternative synthetic procedures for the preparation of the compound which are more amenable to scale-up are desirable.

SUMMARY OF THE INVENTION

The present invention provides an improved processes for the preparation of verubecestat (a Compound of Formula (I)) which may be useful (alone or together with additional active ingredients) in treating, preventing, ameliorating, and/or delaying the onset of an Aβ pathology, including Alzheimer's disease and mild cognitive impairment, and/or a symptom or symptoms thereof. Applicant has found, surprisingly and advantageously, that mixing amine (7) with a weak base (such as sodium bicarbonate or potassium phosphate dibasic) before reacting amine (7) with a cyanating agent significantly increases the yield when compared to reacting an amine (7) with a cyanating agent in the absence of the base.

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

As used herein, and throughout this disclosure, the following terms, unless otherwise indicated, shall be understood to have the following meanings:

The term "alkyl," as used herein, refers to an aliphatic hydrocarbon group having one of its hydrogen atoms replaced with a bond having the specified number of carbon atoms. In different embodiments, an alkyl group contains from 1 to 6 carbon atoms ($C_1$-$C_6$ alkyl) or from 1 to 3 carbon atoms ($C_1$-$C_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched.

The term "haloalkyl," as used herein, refers to an alkyl group as defined above, wherein one or more of the alkyl group's hydrogen atoms has been replaced with a halo. In one embodiment, a haloalkyl group has from 1 to 6 carbon atoms. In another embodiment, a haloalkyl group has from 1 to 3 carbon atoms. In another embodiment, a haloalkyl group is substituted with from 1 to 3 halo atoms. Non-limiting examples of haloalkyl groups include —$CH_2F$, —$CHF_2$, and —$CF_3$. The term "$C_1$-$C_4$ haloalkyl" refers to a haloalkyl group having from 1 to 4 carbon atoms.

The term "alkoxy" as used herein, refers to an —O-alkyl group, wherein an alkyl group is as defined above. Non-limiting examples of alkoxy groups include methoxy, ethoxy, n-propoxy, isopropoxy, n-butoxy and t-butoxy. An alkoxy group is bonded via its oxygen atom to the rest of the molecule.

The term "aryl," as used herein, refers to an aromatic monocyclic or multicyclic ring system comprising from about 6 to about 14 carbon atoms. In one embodiment, an aryl group contains from about 6 to 10 carbon atoms ($C_6$-$C_{10}$ aryl). In another embodiment an aryl group is phenyl. Non-limiting examples of aryl groups include phenyl and naphthyl.

The term "cyanating agent," as used herein, means an electrophilic agent suitable for transferring a cyano group to a nucleophilic reactant and are known to those of ordinary skill in the art. Non-limiting examples of cyanating agents include cyanogen bromide, cyanogen fluoride, cyanogen chloride, cyanogen iodide, 2-methoxyphenyl cyanate, 4-methoxyphenyl cyanate, 4-phenylphenyl cyanate, and bisphenol A cyanate.

The term "Brønsted base," as used herein, means an agent that accepts hydrogen ions during a chemical reaction and are known to those of ordinary skill in the art. Non-limiting examples of Brønsted bases include potassium carbonate, potassium phosphate, cesium carbonate, and potassium bicarbonate.

The term "PG", as used herein in text and in structural depictions of certain compounds herein (e.g., compounds 4, 4A, 6, and 6A), refers to a protecting group. Those skilled in the art will readily envisage protecting groups (PG) suitable for use in the compounds and processes according to the invention. Protecting groups suitable for use herein include acid-labile protecting groups. Non-limiting examples of PG suitable for use herein include —$S(O)_2R^8$, —$C(O)OR^8$, —$C(O)R^8$, —$CH_2OCH_2CH_2SiR^8$ and —$CH_2R_8$ where $R^8$ is selected from the group consisting of —$C_{1-8}$ alkyl (straight or branched), —$C_{3-8}$ cycloalkyl, —$CH_2$(aryl), and —$CH$(aryl)$_2$, wherein each aryl is independently phenyl or naphthyl and each said aryl is optionally independently unsubstituted or substituted with one or more (e.g., 1, 2, or 3) groups independently selected from —OMe, Cl, Br, and I. Preferred protecting groups "PG" include butoxycarbonyl (Boc) and para-methoxybenzyl (PMB).

The term "diazonium group," as used herein, refers to the functional group

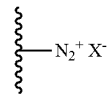

where "<span>∤</span>" indicates the point of attachment to the parent group and X" is an inorganic or organic anion such as a halide.

The term "halo," as used herein, means —F (fluorine), —Cl (chlorine), —Br (bromine) or —I (iodine).

The term "substituted" means that one or more hydrogens on the atoms of the designated moiety are replaced with a selection from the indicated group, provided that the atoms' normal valencies under the existing circumstances are not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

When any substituent or variable occurs more than one time in any constituent or the compound of Formula (I), its definition on each occurrence is independent of its definition at every other occurrence, unless otherwise indicated. For example, description of radicals which include the expression "—N($C_1$-$C_3$ alkyl)$_2$," means —N($CH_3$)($CH_2CH_3$), —N($CH_3$)($CH_2CH_2CH_3$), and —N($CH_2CH_3$)($CH_2CH_2CH_3$), as well as —N($CH_3$)$_2$, —N($CH_2CH_3$)$_2$, and —N($CH_2CH_2CH_3$)$_2$.

It should also be noted that any carbon as well as heteroatom with unsatisfied valences in the text, schemes, examples and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of Formula (I) may contain one or more stereogenic centers and can thus occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

As noted above, verubecestat, alternatively referred to herein as the "Compound of Formula (I)," may exist as either of two tautomeric forms: the "exo" (or "imine") form and the "endo" (or "amine") form, which are shown above. For ease of description, and unless otherwise specified, the expression "a Compound of Formula (I):

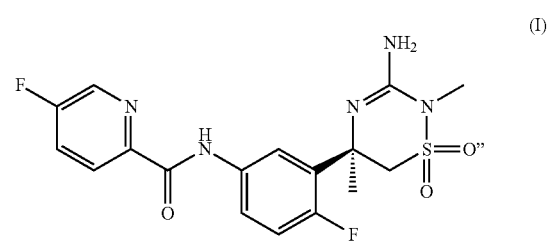

is intended to encompass the endo, or the exo form, or a mixture of both of the endo and exo tautomeric forms.

All stereoisomers (for example, geometric isomers, optical isomers and the like) of the present compounds (including those of the salts and solvates of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

The compounds of Formula (I) and intermediates for the preparation thereof can form salts which are also within the scope of this invention. The term "salt(s)", as employed herein, denotes acidic salts formed with inorganic and/or organic acids, as well as basic salts formed with inorganic and/or organic bases. In addition, when a compound of Formula (I) or a synthetic intermediate contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Such acidic and basic salts used within the scope of the invention are pharmaceutically acceptable (i.e., non-toxic, physiologically acceptable) salts. Salts of the compounds of Formula (I) or a synthetic intermediate may be formed, for example, by reacting a compound of Formula (I) (or synthetic intermediate) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartrates, thiocyanates, toluenesulfonates (also known as tosylates), 1-hydroxy-2-naphthoates (also known as xinafoates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

As used herein, the term "composition" is intended to encompass a product comprising the specified ingredients in the specified amounts, as well as any product which results, directly or indirectly, from combination of the specified ingredients in the specified amounts.

DETAILED DESCRIPTION OF THE INVENTION

The present invention provides an improved processes for the preparation of the Compound of the Formula (I). Thus, in its many embodiments, the present invention provides a processes for the preparation of a compound of Formula (I):

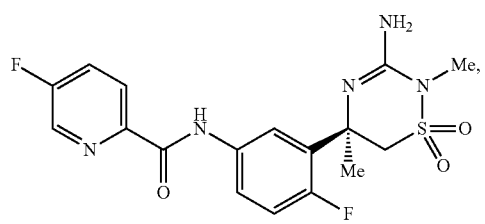

(I)

comprising:
combining an amine

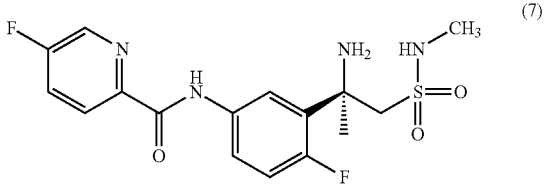 [SMILES: CNS(=O)(=O)C[C@](C)(N)c1cc(NC(=O)c2ccc(F)cn2)ccc1F]

(7)

with a weak base;

then reacting said mixture with a cyanating agent followed by treatment with a Bronsted base to form the compound of Formula (I).

Applicant has found, surprisingly and advantageously, that combining an amine (7) with a weak base (such as sodium bicarbonate or potassium phosphate dibasic) before reacting amine (7) with a cyanating agent significantly increases the yield when compared to reacting an amine (7) with a cyanating agent in the absence of the weak base. Non-limiting examples of the reaction according to the invention and comparative data are set forth below.

In one embodiment, the weak base is selected from sodium bicarbonate ($NaHCO_3$) and potassium phosphate dibasic ($K_2HPO_4$) or mixtures thereof. In another embodiment, the weak base is sodium bicarbonate.

In another embodiment, the amine (7) is dissolved in a solvent prior to the addition of the weak base. In one such embodiment, the solvent is an organic solvent and water. In one embodiment, the solvent is 2MeTHF and water. Suitable alternative organic solvents, which may be used with or without water, include, but are not limited to, acetonitrile, acetone, toluene, dichloromethane, dichloroethane, dimethyl formamide, dimethylacetamide, dimethylsulfoxide, tetrahydrofuran, chlorobenzene, 1,2-dichlorobenzene, cyclopentylmethyl ether, ethyl acetate, isopropyl acetate, nitromethane, trifluoromethylbenzene, methyl ethyl ketone, DME, 2-methyltetrahydrofuran, pentane, N-methylpyrrolidinone, hexane, and n-heptane, or mixtures thereof. In another embodiment, the solvent is acetonitrile. In an alternative embodiment, the solvent is a mixture of acetonitrile and ethyl acetate. In another alternative embodiment, the solvent is a mixture of acetonitrile and isopropyl acetate.

Suitable cyanating agents include but are not limited to cyanogen bromide, cyanogen fluoride, cyanogen chloride, cyanogen iodide, 2-methoxyphenyl cyanate, 4-methoxyphenyl cyanate, 4-phenylphenyl cyanate, and bisphenol A cyanate. In one embodiment, the cyanating agent is cyanogen bromide.

In one embodiment the reaction is conducted with from 1 to 2 equivalents of cyanogen bromide. In another embodiment, the reaction is conducted with from 1 to 1.7 equivalents of cyanogen bromide. In another embodiment, the reaction is conducted with 1.05 equivalents of cyanogen bromide.

In another embodiment, the reaction of amine (7) with a cyanating agent is conducted at a temperature of from 40 to 100° C. In another embodiment, the reaction temperature is from 45 to 50° C. In another embodiment, the reaction temperature is from 70 to 90° C.

In another embodiment, the reaction of amine (7) with a cyanating agent is conducted in acetonitrile at 70-90° C. with 1 to 2 equivalents of cyanogen bromide. In another embodiment, the reaction is conducted in 2MeTHF and water at a temperature of from 45 to 50° C.

Suitable Bronsted bases include, but are not limited to, sodium hydroxide, sodium bicarbonate, triethylamine, N,N'-diisopropylethylamine, 1,1,3,3-Tetramethylguanidine, potassium fluoride, potassium carbonate, sodium carbonate, potassium tert-butoxide, sodium tert-butoxide, potassium phosphate, potassium dihydrogen phosphate, and potassium hydrogen phosphate. In one embodiment, the Bronsted base is sodium hydroxide.

In an alternative of any of the preceeding embodiments, after the reaction of amine (7) and the cyanating agent is deemed complete, the reaction product may be isolated and, if desired, converted to the corresponding salt or recrystallized from a suitable solvent (or combination of solvents).

The amine (7) can be prepared by the methods described in PCT/US15/044410, which methods are incorporated herein by reference, for use in the process according to the invention. Thus, in one embodiment, amine (7) is prepared by deprotecting a PG-protected sulfonamide

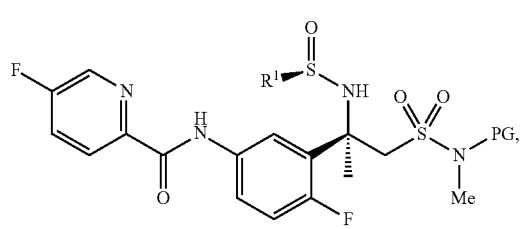

(6)

wherein
R₁ is
C₁-C₆ alkyl; or
phenyl, wherein the phenyl is unsubstituted or substituted by 1 to 3 substituents selected from the group consisting of C₁-C₄ alkyl, C₁-C₄ haloalkyl, —O—C₁-C₄ alkyl, —O—C₁-C₄ haloalkyl, halo, and nitro; and
PG is a protecting group;
with an acid to form the amine (7). In one such embodiment, the PG is butoxycarbonyl (Boc). In another such embodiment, PG is para-methoxybenzyl (PMB). In another such embodiment, the acid is methane sulfonic acid or trifluoroacetic acid. In another alternative of this embodiment, methane sulfonic acid is the acid and the protecting group is PMB.

In another embodiment, the amine (7) is prepared by
deprotecting a PG-protected amine

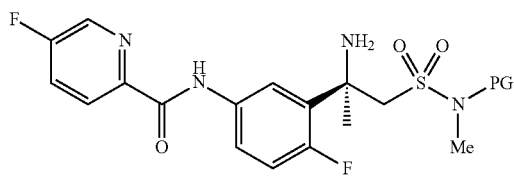

(6A)

with an acid to form the amine (7), wherein PG is a protecting group. In one such embodiment, the PG is butoxycarbonyl (Boc). In another such embodiment, PG is para-methoxybenzyl (PMB). In another such embodiment, the acid is methane sulfonic acid or trifluoroacetic acid. In another alternative of this embodiment, methane sulfonic acid is the acid and the protecting group is PMB.

In another embodiment, the PG-protected sulfonamide (6), and/or the PG-protected amine (6A), is deprotected with 3 to 7 equivalents of the trifluoroacetic acid or with 3 to 7 equivalents of methanesulfonic acid. In another such embodiment, the deprotection is conducted in a solvent selected from the group consisting of acetic acid, toluene, dichloromethane, tetrahydrofuran, isopropyl acetate, dimethylacetamide, N-methylpyrrolidone, cyclopropylmethyl ether, acetonitrile, methyl tert-butyl ether, isopropanol, and mixtures thereof. In an alternative embodiment the solvent is toluene. In another such embodiment, the solvent is toluene and the acid is trifluoroacetic acid. In another alternative, the solvent is acetic acid. In another alternative, the solvent is acetic acid and the acid is methanesulfonic acid. In another embodiment, the deprotection is conducted at 45 to 75° C., for example, at 55 to 65° C.

In another embodiment, the PG-protected sulfonamide (6), or the PG-protected sulfonamide (6A), is deprotected with 3 to 7 equivalents of the trifluoroacetic acid or with 3 to 7 equivalents of the methane sulfonic acid, in toluene, at 45 to 75° C., in toluene, at 45 to 75° C.

In another embodiment, the amine (7) is further purified by:
reacting the amine (7) with an enantiomerically pure chiral acid of the Formula A-H to form a diastereomeric salt mixture;
separating the salt

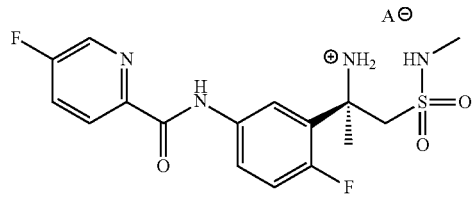

(7A)

from the diastereomeric salt mixture,
reacting the salt (7A) with an aqueous base; and
recovering the free base of amine (7).

In another embodiment, the enantiomerically pure chiral acid of the Formula A-H is selected from the group consisting of L-tartaric acid, L-(+)-mandelic acid, L-(−)-malic acid, (1S)-(+)-10-camphorsulfonic acid, (−)-di-O,O-p-toluyl-L-tartaric acid, (−)-O,O-dibenzoyl-L-tartaric acid, (+)-camphoric acid, L-pyroglutamic acid, (1S)-(−)-camphanic acid, L-valine, (1S)-(+)-3-bromocamphor-10-sulfonic acid hydrate, L-histidine, D-tartaric acid, D-(−)-mandelic acid, D-(+)-malic acid, (1R)-(−)-10-camphorsulfonic acid, (+)-Di-O,O-p-toluyl-D-tartaric acid, (+)-O,O-dibenzoyl-D-tartaric acid, (−)-camphoric acid, D-pyroglutamic acid, (1R)-(+)-camphanic acid, D-valine, (+)-naproxen, and L-isoleucine.

In another embodiment, the aqueous base is sodium carbonate in water.

In another embodiment, the salt (7A) is recovered by isolating the recrystallized salt (7A).

In another embodiment, the PG-protected sulfonamide (6) is prepared by coupling the aryl fluoride

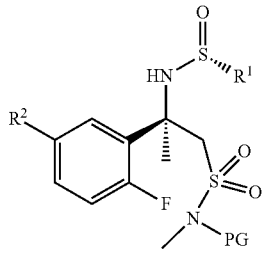

(4)

wherein
R² is halo, selected from the group consisting of bromo, chloro and iodo;

a group of the formula —O—S(O)$_2$—R$^2$, wherein R$^{2a}$ is methyl, chloromethyl, dichloromethyl, phenyl, p-trifluoromethylbenzyl, p-toluenyl, p-bromophenyl, p-fluorophenyl, p-methoxyphenyl, 2-nitrophenyl, 4-nitrophenyl, and 2,4-dichlorophenyl;
or
a diazonium group; and
PG is a protecting group;
with 5-fluoropicolinamide
in the presence of:
a copper or palladium reagent;
a ligand; and
a Brønsted base to form the PG-protected sulfonamide (6). In one such embodiment, PG in compound (4) is butoxycarbonyl (Boc). In another such embodiment, PG in compound (4) is para-methoxybenzyl (PMB).

In another embodiment, the PG-protected amine (6A) is prepared by
coupling the aryl fluoride

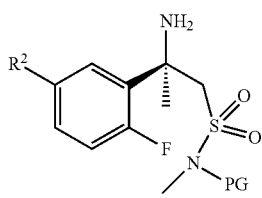

(4A)

or a salt thereof;
wherein R$^2$ is:
halo, selected from the group consisting of bromo, chloro and iodo;
a group of the formula —O—S(O)$_2$—R$^2$, wherein R$^{2a}$ is methyl, chloromethyl, dichloromethyl, phenyl, p-trifluoromethylbenzyl, p-toluenyl, p-bromophenyl, p-fluorophenyl, p-methoxyphenyl, 2-nitrophenyl, 4-nitrophenyl, and 2,4-dichlorophenyl;
or
a diazonium group; and
PG is a protecting group;
with 5-fluoropicolinamide,
in the presence of:
a copper or palladium reagent;
a ligand; and
a Brønsted base to form the PG-protected amine (6A). In one such embodiment, the PG in the compound (4A) is butoxycarbonyl (Boc). In another such embodiment, PG in compound (4A) is para-methoxybenzyl (PMB). In another such embodiment, compound (4A) is in the form of an acid addition salt and PG is Boc or PMB, wherein said acid addition salt is selected from those defined hereinabove. In another embodiment, the aryl fluoride (4A) is in the form of a (−)-O,O-dibenzoyl-L-tartrate salt. In another embodiment, the aryl fluoride (4A) is in the form of a (−)-O,O-dibenzoyl-L-tartrate salt and PG is PMB. In an alternative of the above embodiments, the coupling is conducted with 1 to 3 equivalents of 5-fluoropicolinamide.

In another embodiment, the copper or palladium reagent is selected from the group consisting of CuI, CuI-TBAI, CuBr, CuPF$_6$(MeCN)$_4$, CuBr$_2$, [Cu(OTf)]$_2$-tol, CuCl, Cu metal, Cu$_2$O, Cu(OAc)$_2$, (aminobiphenyl)PdOMs dimer, and (aminobiphenyl)PdCl dimer.

In another embodiment, the copper or palladium reagent is CuI. In another embodiment, said CuI is present at in least 0.01 equivalents. In another such embodiment, said CuI is present in at least 0.2 equivalents. In a non-limiting example, said CuI is present in from 0.01 to 1.4 equivalents. In another example, said CuI is present in from 0.2 to 1.4 equivalents.

In an alternative of the above embodiments, the ligand is selected from the group consist of N,N'-dimethyl diaminocyclohexane, N,N'-dimethylethylenediamine, diaminocyclohexane, tBuBrettphos, DMEDA, Xphos, RuPhos, Sphos, water-soluble Sphos, tBuXPhos, Rockphos, Brettphos, AdBrettphos, Qphos, MorDalphos, Amphos, CataCXiumA, tBu$_3$P, Cy$_3$P, MeCgPPh, o-tol3P, PPh$_3$, BINAP, dppf, dtbpf, Josiphos SL-J009, Johnphos, Xantphos, and NiXantphos. In one such embodiment, the ligand is N,N'-dimethyldiaminocyclohexane or N,N'-dimethylethylenediamine.

In another embodiment, the Brønsted base is selected from the group consisting of potassium carbonate, potassium phosphate, cesium carbonate, and potassium bicarbonate. In one such embodiment, the Brønsted base is potassium carbonate.

In another embodiment, the coupling is conducted in a high boiling organic solvent. For example, the coupling is conducted in a solvent selected from the group consisting of toluene, dimethylacetamide, t-amyl alcohol, and cyclopentyl methyl ether. In another embodiment, the high boiling solvent is toluene.

In another embodiment, the coupling is conducted at 70 to 130° C., for instance, at 80 to 110° C.

In another embodiment, the coupling is optionally conducted in the presence of an additive selected from the group consisting of NaI, KI, I$_2$ and TBAI.

In another embodiment, the copper or palladium reagent is CuI present at 0.01 to 1.4 equivalents, the ligand is N,N'-dimethyldiaminocyclohexane, and the Brønsted base is potassium carbonate. In one such embodiment, the coupling is conducted in toluene at 70 to 130° C.

In another embodiment, the amine (7) is further purified by separating the R-enantiomer from the mixture of enantiomers. In one such embodiment, the separation of the R-enantiomer of the amine (7) from the mixture comprises recrystallization. Suitable recrystallization solvents for this separation include, for example, a mixture of acetonitrile/methyl tert-butyl ether, and toluene (neat). The separation of the R-enantiomer of the amine (7) from the mixture can also be performed using chromatography on a chiral solid-phase media.

In another embodiment, the aryl fluoride (4) or aryl fluoride (4A) is prepared by:
treating the methylsulfonamide

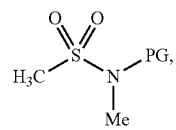

(3)

wherein PG is a protecting group, with an alkali metal base to form the alkali metalate species of the methylsulfonamide (3); and
reacting the alkali metalate species of the methylsulfonamide (3) with sulfinyl imine

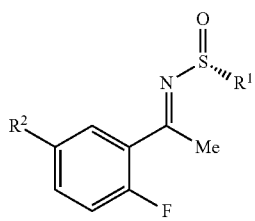

(2)

to form the aryl fluoride (4). In one such embodiment, PG is Boc. In another such embodiment, PG is PMB. In the aforementioned alternative embodiment above, the aryl fluoride (4) is further treated with a strong acid to form (4A). Suitable strong acids will be readily apparent to those of ordinary skill in the art. Non-limiting examples of such acids include, but are not limited to, mandelic acid, hydrochloric acid, hydrobromic acid, methanesulfonic acid, tetrafluoroboric acid, trifluoromethane sulfonic acid, sulfuric acid, fumaric acid, and citric acid. In one such embodiment, the strong acid is mandelic acid. In another such embodiment, the strong acid is hydrochloric acid. In one embodiment, the aryl fluoride (4) is produced according to the aforementioned process in the absence of treating with an acid. In another alternative of each of the immediately preceeding embodiments. PG is PMB.

In another embodiment, the alkali metal base is selected from the group consisting of n-HexLi, n-BuLi, KHMDS, and NaHMDS. In one such embodiment, the alkali metal base is n-BuLi. In an alternative embodiment, the alkali metal base is n-hexLi.

In one embodiment, the treatment with the alkali metal base and reaction with the sulfinyl imine (2) is conducted in an organic solvent selected from the group consisting of dichloromethane, tetrahydrofuran, 2-methyltetrahydrofuran, toluene, cyclopentylmethyl ether, and dimethoxyethane. In one such embodiment, the organic solvent is tetrahydrofuran.

In one embodiment, the treatment with the alkali metal base and reaction with the sulfinyl imine (2) is optionally conducted in the presence of an additive selected from the group consisting of $MgCl_2$, $ZnCl_2$, $Al(O-iPr)_3$, $In(OTf)_3$, $FeCl_2$, $CuBr$, $CuBr_2$, $SnCl_2$, $Sc(OTf)_3$, $Fe(acac)_3$, $BF_3 \cdot OEt_2$, $Ti(OEt)_4$, TMSOTf, TMEDA, HMPA and LiCl.

In one embodiment, the alkali metal base is n-BuLi and the treatment with the alkali metal base and reaction with the sulfinyl imine (2) is conducted in THF. In an alternative embodiment, the alkali metal base is n-HexLi and the treatment with the alkali metal base and reaction with the sulfinyl imine (2) is conducted in THF.

In one embodiment, the sulfinyl imine (2) is prepared by:
condensing ketone

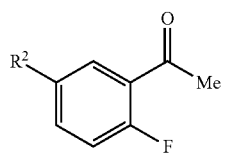

(10)

with
a sulfinamide of the formula $R^1$—S(O)—$NH_2$ (11) in the presence of a tetra($C_1$-$C_6$ alkoxy)titanium (IV) or tetra($C_1$-$C_6$ alkoxy)zirconium (IV) catalyst to form sulfinyl imine (2).

In one embodiment, the condensation catalyst is titanium (IV) ethoxide.

In one embodiment, the condensation is conducted in a solvent selected from the group consisting of ethyl acetate, acetone, toluene, dichloromethane, dichloroethane, dimethylformamide, dimethylacetamide, dimethylsulfoxide, tetrahydrofuran, chlorobenzene, 1,2-dichlorobenzene, cyclopentylmethyl ether, acetonitrile, isopropyl acetate, nitromethane, trifluoromethyl benzene, methyl ethyl ketone, dimethoxyethane, 2-methyltetrahydrofuran, pentane, N-methylpyrrolidone, hexane and n-heptane. In one embodiment, the solvent for the condensation is ethyl acetate.

In one embodiment, the catalyst is titanium (IV) ethoxide and the condensation is conducted in ethyl acetate. In one such embodiment, the condensation is conducted at 40 to 70° C.

In one embodiment, the PG-protected sulfonamide (6) or the PG-protected amine (6A) is prepared by:
treating the methylsulfonamide

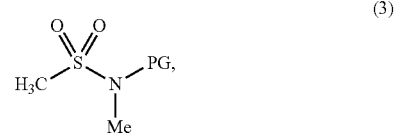

(3)

wherein PG is a protecting group, with an alkali metal reagent to form the alkali metalated species of the methylsulfonamide (3); and
reacting the alkali metalated species of the methylsulfonamide (3) with sulfinyl imine

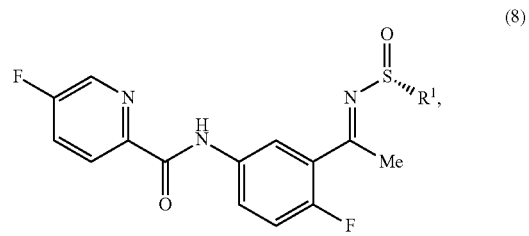

(8)

wherein
$R_1$ is
$C_1$-$C_6$ alkyl; or
phenyl, wherein the phenyl is unsubstituted or substituted by 1 to 3 substituents selected from the group consisting of $C_1$-$C_4$ alkyl, $C_1$-$C_4$ haloalkyl, —O—$C_1$-$C_4$ alkyl, —O—$C_1$-$C_4$ haloalkyl, halo, and nitro;
to form the PG-protected sulfonamide (6), which can be further treated with a strong acid to form the PG-protected amine (6A). Suitable strong acids will be readily apparent to those of ordinary skill in the art. Non-limiting examples of such acids include, but are not limited to, hydrochloric acid, hydrobromic acid (HBr), methanesulfonic acid, tetrafluoroboric acid, trifluoromethane sulfonic acid, sulfuric acid, fumaric acid, and citric acid. In one such embodiment, the strong acid is hydrochloric acid (HCl). In one such embodiment, PG-protected sulfonamide (6) is produced according to the aforementioned process in the absence of treating with an acid. In an alternative of each of the immediately preceeding embodiments, PG is PMB.

In one embodiment, the alkali metal base is selected from the group consisting of n-HexLi, n-BuLi, KHMDS, and NaHMDS. In one such embodiment, the alkali metal base is n-BuLi. In an alternative such embodiment, the alkali metal base is n-hexLi.

In one embodiment, the treatment with the alkali metal base and reaction with the sulfinyl imine (8) is conducted in an organic solvent selected from the group consisting of dichloromethane, tetrahydrofuran, 2-methyltetrahydrofuran, toluene, cyclopentylmethyl ether, and dimethoxyethane. In one such embodiment, the organic solvent is dichloromethane.

In one embodiment, the treatment with the alkali metal base and reaction with the sulfinyl imine (8) is optionally conducted in the presence of an additive selected from the group consisting of $MgCl_2$, $ZnCl_2$, $Al(O-iPr)_3$, $In(OTf)_3$, $FeCl_2$, $CuBr$, $CuBr_2$, $SnCl_2$, $Sc(OTf)_3$, $Fe(acac)_3$, $BF_3 \cdot OEt_2$, $Ti(OEt)_4$, TMSOTf, TMEDA, HMPA and LiCl.

In one embodiment, the alkali metal base is n-BuLi and the treatment with n-BuLi and reaction with the sulfinyl imine (8) is conducted in dichloromethane. In an alternative such embodiment, the alkali metal base is n-HexLi.

In one embodiment, the sulfinyl imine (8) is prepared by condensing ketone

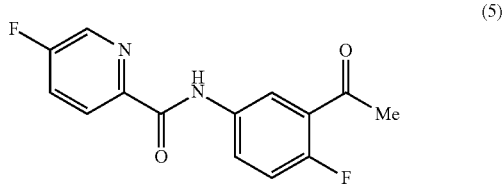 [SMILES: CC(=O)c1cc(NC(=O)c2ccc(F)cn2)ccc1F]

(5)

with a sulfinamide of the formula $R^1$—S(O)—$NH_2$ (11) in the presence of a tetra($C_1$-$C_6$ alkoxy)titanium (IV) catalyst to form sulfinyl imine (8).

In one embodiment, the catalyst is $Ti(OEt)_4$ and the condensation is conducted in tetrahydrofuran.

In one embodiment, the ketone (5) is prepared by coupling ketone

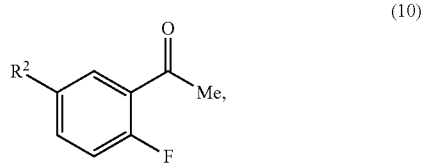

(10)

wherein R is:
(i) halo, selected from the group consisting of bromo, chloro and iodo;
(ii) a group of the formula —O—S(O)$_2$—$R^{2a}$, wherein $R^{2a}$ is methyl, chloromethyl, dichloromethyl, phenyl, p-trifluoromethylbenzyl, p-toluenyl, p-bromophenyl, p-fluorophenyl, p-methoxyphenyl, 2-nitrophenyl, 4-nitrophenyl, and 2,4-dichlorophenyl; or
(iii) a diazonium group;
with 5-fluoropicolinamide, in the presence of:
a copper reagent;
a ligand; and
a Brønsted base;
to form the ketone (5).

In one embodiment, the copper reagent is selected from the group consisting of CuI, CuI-TBAI, $Cu(TMHD)_2$, $Cu(AcChxn)_2$, and $Cu(iBuChxn)_2$. In one such embodiment, the copper reagent is CuI.

In one embodiment, the ligand is selected from the group consisting of DMEDA, DACH, DM-DACH, N,N-dimethylglycine, TMEDA, bipyridine, 4,4-di-tBubipy, phenanthroline, neocuprine, tetramethylphenanthroline, terpyridine, tri-T-tBu-typyridine, 8-hydroxyquinoline, proline, picolinic acid, thiophene-2-carboxylic acid, N,N-diethylsalicylamide, SALOX, Chxn-Py-Al, 1,3-di(2-pyridyl)-1,3-propanedione, TMHD, AcChxn, and iBuChxn. In such embodiment, the ligand is selected from the group consisting of DMEDA, DACH, DM-DACH, and N,N-dimethylglycine.

In one embodiment, the Brønsted base is selected from the group consisting of potassium carbonate, cesium carbonate, and potassium phosphate.

In one embodiment, the coupling is conducted in a solvent selected from the group consisting of toluene and DMSO.

In one embodiment, the ketone (5) is prepared by coupling 1-(5-amino-2-fluorophenyl)ethanone with 5-fluoropicolinic acid.

In one embodiment, the the coupling is conducted with a coupling agent selected from propylphosphonic anhydride ($T_3P$), DCC and EDC.

In one embodiment, the amine (7) is prepared by coupling the amine

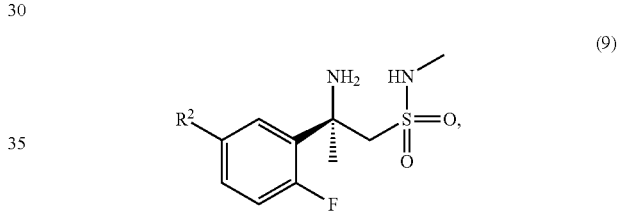

(9)

wherein $R^2$ is:
(i) halo, selected from the group consisting of bromo, chloro and iodo;
(ii) a group of the formula —O—S(O)$_2$—$R^{2a}$, wherein $R^{2a}$ is methyl, chloromethyl, dichloromethyl, phenyl, p-trifluoromethylbenzyl, p-toluenyl, p-bromophenyl, p-fluorophenyl, p-methoxyphenyl, 2-nitrophenyl, 4-nitrophenyl, and 2,4-dichlorophenyl; or
(iii) a diazonium group;
with 5-fluoropicolinamide in the presence of:
a metal reagent selected from the group consisting of a palladium reagent and a copper reagent
a ligand; and
a Brønsted base.

In one such embodiment, the metal reagent is selected from the group consisting of CuI-TBAI, CuBr, $CuPF_6(CH_3CN)_4$, $CuBr_2$, $[Cu(OTf))]_2$-tol, CuCl, CuI, CuBr-DMS, (aminobiphenyl)PdOMs dimer, and (aminobiphenyl)PdCl dimer. In another such embodiment, the metal reagent is a palladium reagent selected from the group consisting of (aminobiphenyl)PdOMs dimer, and (aminobiphenyl)PdCl dimer.

In one embodiment, the ligand is selected from the group consisting of N,N'-dimethyl diaminocyclohexane, diaminocyclohexane, DMEDA, Rockphos, tBuBrettphos, AdBrettphos, Xphos, RuPhos, Sphos, water-soluble Sphos, tBuXPhos, Brettphos, Qphos, MorDalphos, Amphos, CataCXiumA, tBu₃P, Cy₃P, MeCgPPh, o-tol3P, PPh₃, BINAP, dppf, dtbpf, Josiphos SL-J009, Johnphos, Xantphos, and NiXantphos.

In one embodiment, the coupling is conducted in a solvent selected from the group consisting of 2-methyltetrahydrofuran, toluene, dimethylacetamide, t-amyl alcohol, and cyclopentyl methyl ether.

In one embodiment, the amine (9) is prepared by deprotecting the aryl fluoride (4) or by deprotecting the aryl fluoride (4A) with trifluoroacetic acid to form the amine (9). For example, the aryl fluoride (4) or the aryl fluoride (4A) is reacted with 3 to 7 equivalents of the trifluoroacetic acid.

In one embodiment, the deprotection is conducted in a solvent selected from the group consisting of toluene toluene, dichloromethane, tetrahydrofuran, isopropyl acetate, dimethylacetamide, N-methylpyrrolidone, cyclopropylmethyl ether, acetonitrile, methyl tert-butyl ether, and isopropanol. In another such embodiment, the deprotection is conducted at 45 to 75° C., for instance, at 55 to 65° C.

In one embodiment, the aryl fluoride (4) or the aryl fluoride (4A) is reacted with 3 to 7 equivalents of the trifluoroacetic acid, the deprotection is conducted in a solvent and at a temperature as set forth above.

In an alternative of any of the preceeding embodiments, $R^1$ is tert-butyl.

In an alternative of any of the preceeding embodiments, $R^2$ is bromo.

In an alternative of any of the preceeding embodiments, $R^1$ is tert-butyl and $R^2$ is bromo.

The following schemes further illustrate the processes of the invention. The variables $R^1$ and $R^2$ in the schemes are as set forth in the embodiment described above. In the schemes and preparative examples that follow, the protecting group (where present) is depicted as PMB (para-methoxybenzyl). However, it shall be understood that, in each occurrence, PMB may be substituted with Boc or any other suitable protecting group PG, examples of which will be readily apparant to those of ordinary skill in the art. Additional non-limiting examples of suitable protecting groups include —S(O)₂R⁸, —C(O)OR⁸, —C(O)R⁸, —CH₂OCH₂CH₂SiR⁸ and —CH₂R₈ where R⁸ is selected from the group consisting of —C₁₋₈ alkyl (straight or branched), —C₃₋₈ cycloalkyl, —CH₂(aryl), and —CH(aryl)₂, wherein each aryl is independently phenyl or naphthyl and optionally substituted with one or more (e.g., 1, 2, or 3) groups independently selected from —OMe, Cl, Br, and I, as described hereinabove.

Scheme I shows one embodiment of the invention wherein the compound of the Formula (I) is prepared.

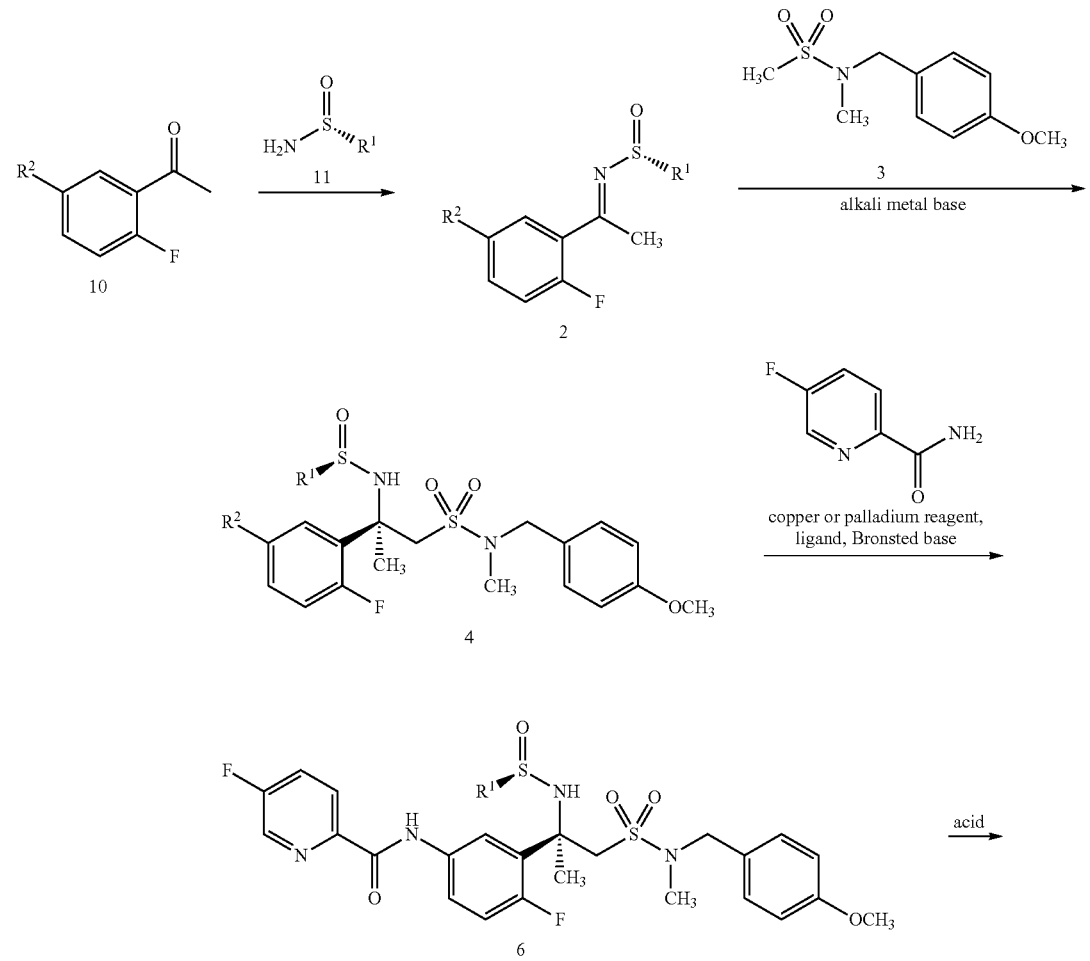

Scheme 1

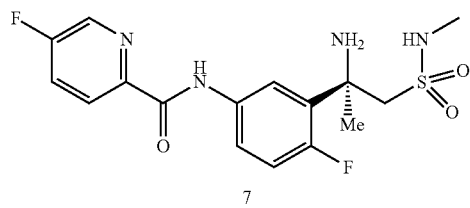
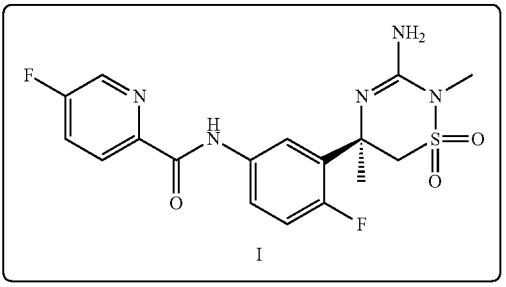

As shown in Scheme 1, substituted ketone (10) is condensed with a sulfonamide (11) to form sulfinyl imine (2). The sulfinyl imine (2) is reacted with an alkali-metalated species of the methyl sulfonamide (3) to form the aryl fluoride (4). In order to prepare the PMB-protected sulfonamide (6), the aryl fluoride (4) is coupled with a copper or palladium reagent, a ligand, and a Brønsted base. The PMB-protected sulfonamide (6) is deprotected with methanesulfonic acid to provide the amine (7). Ring cyclization is accomplished by mixing amine (7) with a weak base (such as sodium bicarbonate or potassium phosphate dibasic), optionally in the presence of an organic solvent and water, then reacting amine (7) with a cyanating agent followed by a Brønsted base.

The following schemes, described in PCT application No. PCT/US15/044410, filed Aug. 10, 2015, set forth a preparation of amine (7) and precursors thereof.

Scheme 2 illustrates an alternative process for preparing the amine (7).

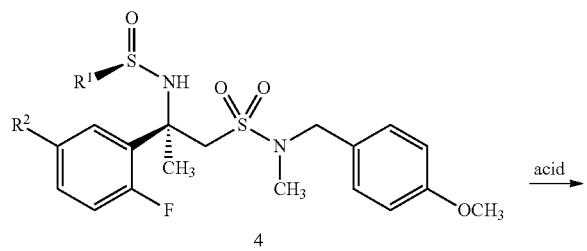

As shown in Scheme 2, the aryl fluoride (4) is deprotected with an acid such as methanesulfonic acid to provide the amine (9). Coupling of (9) with 5-fluoropicolinamide in the presence of a copper or palladium reagent, a ligand and a Brønsted base provides the amine (7).

Scheme 3 illustrates an alternative process for preparing the amine (6) or (6A).

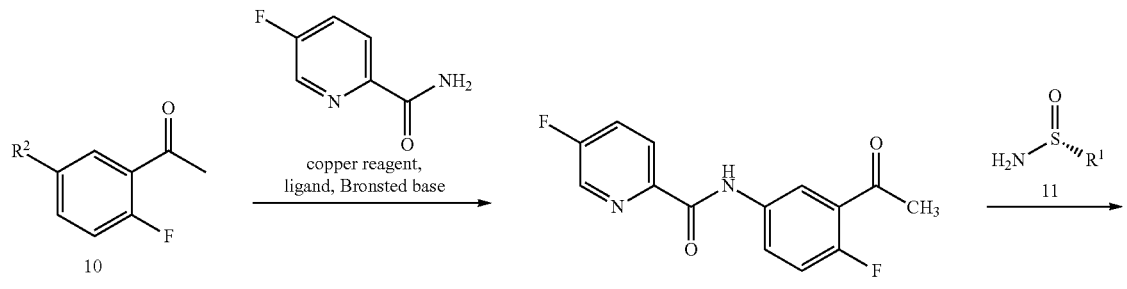

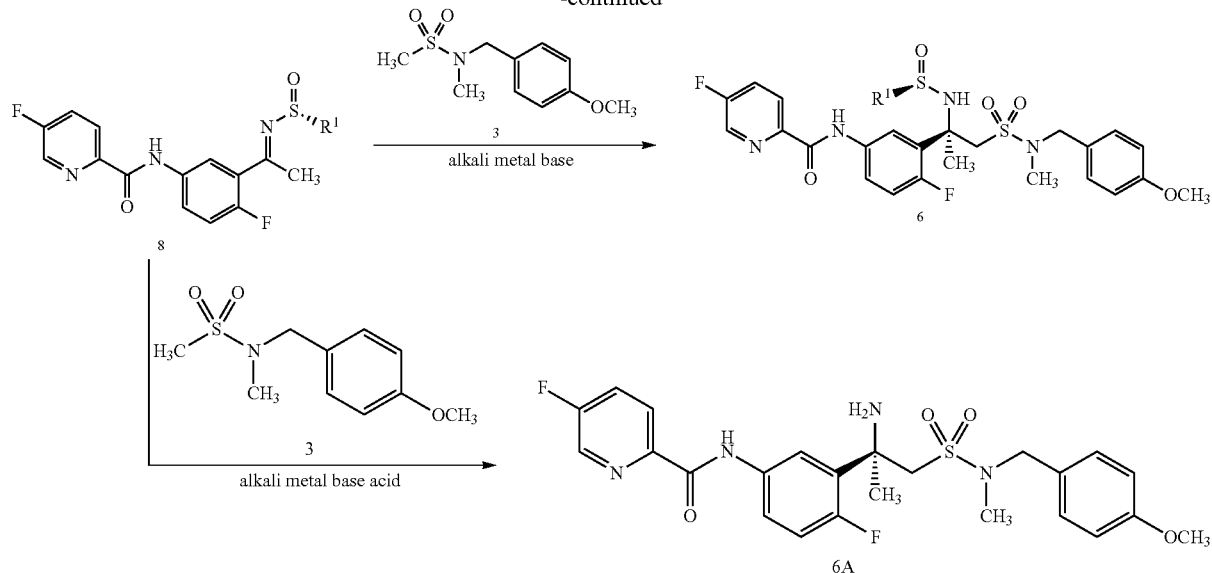

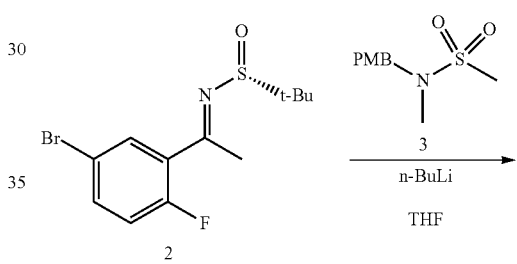

As shown in Scheme 3, coupling of ketone (10) in the presence of a copper reagent, a ligand, and a Brønsted base to provide the ketone (5), which can be condensed with sulfonamide (11) to yield the sulfinyl imine (8). To prepare the PMB-protected sulfonamide (6), sulfinyl imine (8) is reacted with an alkali metalated species of methylsulfonamide (3). Alternatively, to prepare the PMB-protected amine (6A), sulfinyl imine (8) is reacted with an alkali metalated species of methylsulfonamide (3) followed by an acid.

Scheme 4 illustrates an alternative process for preparing the ketone (5).

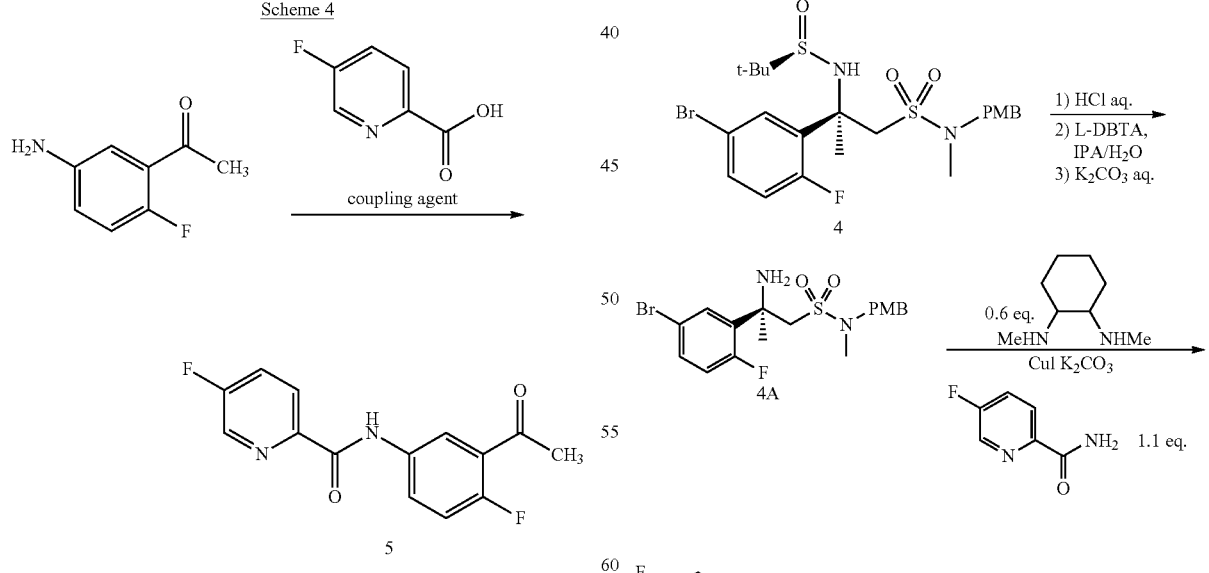

As shown in Scheme 4, ketone (5) is prepared by coupling 1-(5-amino-2-fluorophenyl)ethanone acid with 5-fluoropicolinic acid. Typically, the coupling is carried using a coupling agent such as T₃P, DCC or EDC.

Scheme 5 illustrates another alternative process for preparing the amine (7).

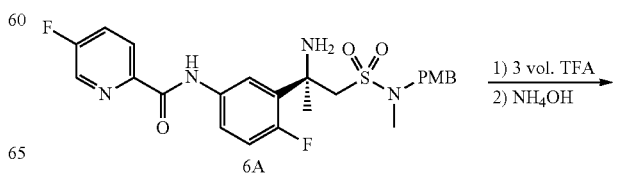

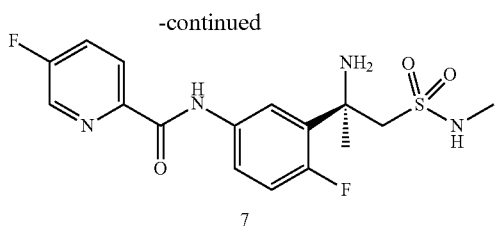

7

As shown in Scheme 5, the sulfinyl imine (2) is reacted with an alkali-metalated species of the methyl sulfonamide (3) followed by an acid such as tartaric acid to form the aryl fluoride (4). The PMB-protected amine (6A) is prepared by coupling a aryl fluoride (4A) with 5-fluoropicolinamide in the presence of a copper or palladium reagent, a ligand, and a Brønsted base. Suitable ligands include N,N'-dialkyl-containing ligands. Non-limiting examples of such ligands include trans-N,N'-dimethylcyclohexane-1,2-diamine (pictured in Scheme 5 and Example 6) and N,N'-dimethylethylene-1,2-diamine. The PMB-protected amine (6A) is deprotected with an acid such as trifluoroacetic acid to provide the amine (7).

PREPARATIVE EXAMPLES

Methods for preparing the Compound of Formula (I) are exemplified below. Starting materials are made according to procedures known in the art or as illustrated herein.

Certain starting materials can be prepared according to procedures known in the art. For example, 1-(5-bromo-2-fluorophenyl)ethanone (10a) can be prepared as described in U.S. Patent Application Publication No. 2003/0187026. (R)-2-methylpropane-2-sulfinamide can be prepared as described in as described in Liu, Guangcheng et al., *Journal of the American Chemical Society*, 119(41), 9913-9914; 1997. 4-Methoxybenzaldehyde can be prepared as described in Adams, Roger et al., *Journal of the American Chemical Society*, 46, 1518-21; 1924. 1-(5-Amino-2-fluorophenyl)ethanone can be prepared as described in Culbertson, Townley P. et al., *Journal of Heterocyclic Chemistry*. 24(6), 1509-20; 1987. 5-Fluoropicolinamide can be prepared as described in International Patent Application Publication No. WO 2003/015776. 5-Fluoropicolinic acid can be prepared as described in U.S. Pat. No. 4,798,619.

ABBREVIATIONS

NaHCO₃: sodium bicarbonate
K₂HPO₄: potassium phosphate dibasic
g: grams
mg: milligrams
mL: milliliters
mmol: millimoles
r.t.: room temperature
h: hours
min: minutes
Me: methyl
Et: ethyl
Pr: propyl
iPr: isopropyl
iPrAc: isopropyl acetate
Bu: butyl
tBu: tert-butyl
Ph: phenyl
Bn: benzyl
OAc: acetate
tol: tolyl
Tf: trifluoromethanesulfonyl
PMB: p-methoxybenzyl
Ms: methanesulfonyl
EtOAc: ethyl acetate
THF: tetrahydrofuran
2MeTHF (or 2-Me-THF): 2-methyltetrahydrofuran
MeCN: acetonitrile
CPME: cyclopentylmethyl ether
HMDS: hexamethyldisilazane
HMPA: hexamethylphosphoramide
TFA: trifluoroacetic acid
TBAI: tetrabutylammonium iodide
DCC: 1,3-dicyclohexylcarbodiimide
EDC: 1-ethyl-3-(3-dimethylaminopropyl)carbodiimide
T₃P: propylphosphonic anhydride
DMS: dimethylsulfide
TMSOTf: trimethylsilyl trifluoromethanesulfonate
DACH: 1,2-diaminocyclohexane
DMEDA: N,N'-dimethylethylenediamine
DM-DACH: trans-N,N'-dimethylcyclohexane-1,2-diamine
TBAI: tetrabutylammonium iodide
aminobiphenylPdOMs: aminobiphenylmethanesulfonate
Dba: dibenzylideneacetone
TMHD: 2,2,6,6-tetramethyl-3,5-heptanedionate
AcChxn: 2-acetylcyclohexanone
iBuChxn: 2-isobutyrylcyclohexanone
TMEDA: Tetramethylethylenediamine
Rockphos: 2-di(tert-butyl)phosphino-2',4',6'-triisopropyl-3-methoxy-6-methylbiphenyl
tBuBrettphos: 2-(di-tert-butylphosphino)-2',4',6'-triisopropyl-3,6-dimethoxy-1,1'-biphenyl
AdBrettphos: di((adamantan-1-yl)(2',4',6'-triisopropyl-3,6-dimethoxy-[1,1'-biphenyl]-2-yl)phosphine
Xphos: 2-dicyclohexylphosphino-2',4',6'-triisopropylbiphenyl
tBu₃P: tri-tert-butyl phosphine
Dtbpf: 1,1'-bis(di-tert-butylphosphino)ferrocene
tBuXPhos: 2-di-tert-butylphosphino-2',4',6'-triisopropylbiphenyl
Qphos: 1,2,3,4,5-pentaphenyl-1'-(di-tert-butylphosphino)ferrocene
tBuBippyphos: 5-(di-tert-butylphosphino)-1',3',5'-triphenyl-1'H-[1,4']bipyrazole
Bippyphos: 5-(di-tert-butylphosphino)-1',3',5'-triphenyl-1'H-[1,4']bipyrazole
AdBippyphos (Adamantyl-BippyPhos): 5-[di(1-adamantyl)phosphino]-1',3',5'-triphenyl-1'H-[1,4']bipyrazole
Xphos: 2-dicyclohexylphosphino-2',4',6'-triisopropylbiphenyl
Sphos: 2-dicyclohexylphosphino-2',6'-dimethoxybiphenyl
Johnphos: (2-biphenyl)di-tert-butylphosphine
Davephos: 2-dicyclohexylphosphino-2'-(N,N-dimethylamino)biphenyl
RuPhos: 2-dicyclohexylphosphino-2',6'-diisopropoxybiphenyl
tetramethyl tBuXPhos: 2-di-tert-butylphosphino-3,4,5,6-tetramethyl-2',4',6'-triisopropyl-1,1'-biphenyl
Brettphos: 2-(dicyclohexylphosphino)3,6-dimethoxy-2',4',6'-triisopropyl-1,1'-biphenyl
cataXCium A: di(1-adamantyl)-n-butylphosphine
AmPhos: di-tert-butyl(4-dimethylaminophenyl)phosphine
tBu₂PBu: di-tert-butyl(n-butyl)phosphine Xantphos: 4,5-bis(diphenylphosphino)-9,9-dimethylxanthene
Dppf: 1,1'-bis(diphenyiphosphanyl) ferrocene
Dippf: 1,1'-bis(di-i-propylphosphino)ferrocene
Dppp: propane-1,3-diylbis(diphenylphosphane)
Dppb: 1,4-bis(diphenylphosphino)butane
DPEPhos: bis[(2-diphenylphosphino)phenyl]methane
BINAP: 2,2'-bis(diphenylphosphino)-1,1'-binaphthyl
Josiphos SL-J009: 1-[(SP)-2-(Dicyclohexylphosphino)ferrocenyl]ethyldi-tert-butylphosphine
MorDaiphos: di(1-adamantyl)-2-morpholinophenylphosphine
MeCgPPh=1,3,5,7-tetramethyl-6-phenyl-2,4,8-trioxa-6-phosphaadamantane
cataCXium PtB: N-Phenyl-2-(di-t-butylphosphino)pyrrole
o-Tol$_3$P: tri(o-tolyl)phosphine
Cy$_3$P: tricyclohexylphosphane
tBuXPhos: 2-di-tert-butylphosphino-2',4',6'-triisopropylbiphenyl
Bipyridine: 2,2'-bipyridine
4,4-di-tBubipy: 4,4'-di-tert-butyl-2,2'-bipyridine
Neocuproine: 2,9-dimethyl-1,10-phenanthroline
Tetramethylphenanthroline: 2,3,4,5-Tetramethyl-1,7-phenanthroline
Terpyridine: 2,6-bis(2-pyridyl)pyridine
tri-tBu-terpyridine: 4,4',4"-tri-tert-butyl-2,2':6',2"-terpyridine
8-hydroxyquinoline: 8-quinolinol
SALOX: 2-hydroxybenzaldehyde oxime
Chxn-Py-Al: $N^1,N^2$-bis(pyridin-2-ylmethylene)cyclohexane-1,2-diamine
TMHD: 2,2,6,6-tetramethyl-3,5-heptanedione
DMPAO: (2,6-dimethylanilinoXoxo)acetic acid
DMeOPAO: 2-((2,6-dimethoxyphenyl)amino)-2-oxoacetic acid
DCF$_3$PAO: 2-((3,5-bis(trifluoromethyl)phenyl)amino)-2-oxoacetic acid
TBPmalonate: tetrabutylphosphonium malonate (2 phosphonium units)
tBu-TMG: 2-tert-butyl-1,1,3,3-tetramethylguanidine
TMG: N,N,N',N'-tetramethylguanidine
n-BuLi: n-butyllithium
n-HexLi: n-hexyllithium The following examples are provided so that the invention may be more fully understood. These examples are illustrative only and should not be construed as limiting the invention in any way.

Nuclear magnetic resonance (NMR) spectra were recorded for $^1$H NMR at 500 MHz or 400 MHz. Chemical shifts were reported in ppm relative to the residual deuterated solvent for $^1$H. Splitting patterns for $^1$H NMR signals are designated as: s (singlet), d (doublet), t (triplet), q (quartet), quint (quintuplet), broad singlet (br s) or m (multiplet).

Example A

Example A provides one embodiment of the improved process according to the invention, wherein the amine (7) is treated with a weak base (such as sodium bicarbonate or potassium phosphate dibasic) prior to reacting amine (7) with a cyanating agent.

Step 1: Preparation of Verubecestat (I)

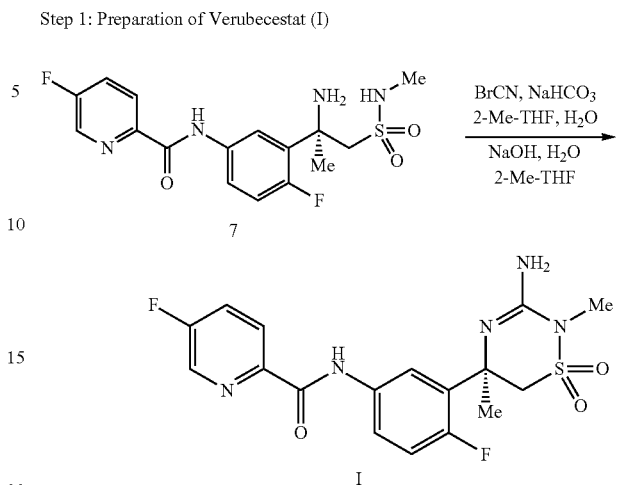

To a reactor (R-1) equipped with a temperature probe, nitrogen inlet, and agitator was charged (R)—N-(3-(2-amino-1-(N-methylsulfamoyl)propan-2-yl)-4-fluorophenyl)-5-fluoropicolinamide (7) followed by 2-Me-THF (5 volumes) and water (0.5 volumes). Agitation was begun and NaHCO$_3$ (1 equivalent) was added followed by BrCN (5 M in MeCN, 1.05 equivalents) was charged. The slurry was heated to 45-50° C. and the resulting homogeneous solution was agitated until the reaction was deemed complete. The reaction was cooled to ambient temperature and diluted with water. After agitating for 30 minutes the water layer was removed and the organic layer was treated with IM aqueous NaOH (1 equivalent). After the reaction was deemed complete the aqueous layer was removed dried over MgSO$_4$, filtered, and concentrated. The solids were dissolved in iPrOAc and heated to 40-50° C. Heptane was charged followed by a small amount of crystalline seeds of I. Additional heptane was added over 4 h and the slurry cooled to ambient temperature. The solids were collected, washed with heptane (26 mL), and dried under vacuum with a N$_2$ sweep to afford I. $^1$H NMR (CDCl$_3$, 400 MHz) 9.69 (s, 1H), 8.20-8.32 (m, 2H), 7.99 (m, 1H), 7.52-7.66 (m, 2H), 7.07 (m, 1H), 5.33 (s, 2H), 3.97 (d, J=13.9 Hz, 1H), 3.67 (d, J=14.0 Hz, 1H), 3.22 (s, 3H), 1.79 (s, 3H); MS (m/z): [M+H]$^+$ calcd for C$_{17}$H$_{18}$F$_2$N$_5$O$_5$S, 410.11; found, 410.03.

Comparative Example A

The following comparative example illustrates the process of Example A wherein an amine (7) is reacted with a cyanating agent without the prior treatment with a weak base.

Step 1: Preparation of Verubecestat (I)

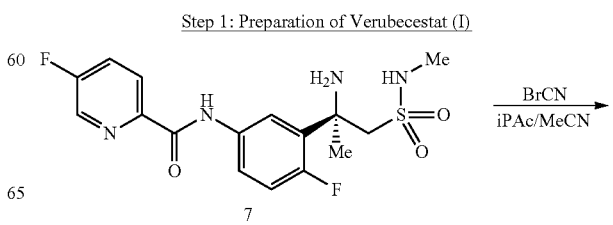

-continued

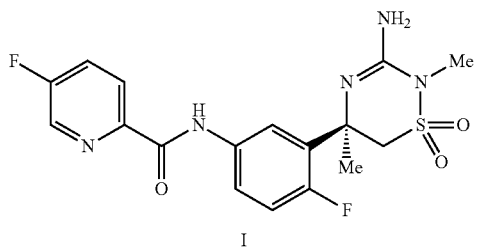

I

To a reactor (R-1) equipped with a temperature probe, nitrogen inlet, and agitator was charged (R)—N-(3-(2-amino-1-(N-methylsulfamoyl)propan-2-yl)-4-fluorophenyl)-5-fluoropicolinamide (7) (8.10 g, 21.1 mmol) followed by a 7:3 mixture of iPAc and MeCN (40.5 mL). Agitation was begun and then BrCN (5 M in MeCN, 6.32 mL, 31.6 mmol) was charged. The slurry was heated to 80-90° C. and the resulting homogeneous solution was agitated until the reaction was deemed complete. The reaction was cooled to ambient temperature and diluted with EtOAc (122 mL). The organics were washed twice with saturated aqueous $NaHCO_3$ (2×80 mL), dried over $MgSO_4$, filtered, and concentrated. The solids were dissolved in EtOAc (52 mL) and heated to 40-50° C. Heptane (8.6 mL) was charged followed by a small amount of crystalline seeds of I. Additional heptane (69 mL) was added over 4 h and the slurry cooled to ambient temperature. The solids were collected, washed with heptane (26 mL), and dried under vacuum with a $N_2$ sweep to afford I (2.89 g, 7.06 mmol). $^1$H NMR ($CDCl_3$, 400 MHz) δ 9.69 (s, 1H), 8.20-8.32 (m, 2H), 7.99 (m, 1H), 7.52-7.66 (m, 2H), 7.07 (m, 1H), 5.33 (s, 2H), 3.97 (d, J=13.9 Hz, 1H), 3.67 (d, J=14.0 Hz, 1H), 3.22 (s, 3H), 1.79 (s, 3H); MS (m/z): $[M+H]^+$ calcd for $C_{17}H_{18}F_2N_5O_5S$, 410.11; found, 410.03.

As noted above, Applicant has found, surprisingly and advantageously, that the addition of a weak base (such as sodium bicarbonate or potassium phosphate dibasic) prior to reacting amine (7) with a cyanating agent followed by treatment with a Bronsted base significantly increases the yield when compared to reacting an amine (7) with a cyanating agent and a Bronsted base without prior treatment with the weak base. The Table below reports the yields (conversion rate of amine (7) to compound of Formula (I)) obtained by the procedures described in Example A and Comparative Example A, respectively.

| Example | Conditions | Conversion to I |
|---|---|---|
| Example A | BrCN, iPAc/MeCN (7/3), 80-90° C. | 70% |
| Comparative Example A | BrCN, $NaHCO_3$, 2-Me—THF, $H_2O$, 45-50° C., then NaOH | >99% |

The following examples, described in PCT application No. PCT/US15/044410, filed Aug. 10, 2015, set forth a preparation of amine (7) and precursors thereof.

Example 1

Step A: Preparation of (R,E)-N-(1-(5-bromo-2-fluorophenyl)ethylidene)-2-methylpropane-2-sulfinamide (2a)

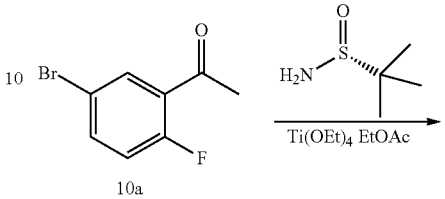

2a

To a reactor (R-1) equipped with a temperature probe, nitrogen inlet and agitator was charged 1-(5-bromo-2-fluorophenyl)ethanone (95%, 9.3 g, 40.7 mmol) and (R)-2-methylpropane-2-sulfinamide (5.4 g, 44.6 mmol). Next, ethyl acetate was charged to the reactor (47 mL). Agitation was begun and the reaction was warmed to 50 to 70° C. titanium (IV) ethoxide (10 mL, 40.7 mmol) was charged to the reaction, and the reaction was allowed to agitate at 50 to 70° C. When the reaction was deemed complete, the reaction was cooled to 20 to 30° C.

In a separate reactor (R-2) equipped with an agitator was charged sodium bicarbonate (6.5 g, 77 mmol) and water (90 mL). The contents of R-2 were agitated until all solids had dissolved. Next, CELITE (10 g) was charged to the vessel. The contents of reactor R-1 were added to reactor R-2. Upon complete addition, the reaction was allowed to agitate at 20 to 30° C. At this point, the reaction was filtered and the filtrate containing 2a was charged into a new reactor (R-3). The aqueous later was separated and extracted with 30 mL ethyl acetate. The organic layers were combined and washed with 30 mL of a saturated aqueous sodium chloride solution. The organic layer was then separated and concentrated to about 20 mL total volume. 80 mL n-heptane was charged to the reactor and concentrated the solution to a total volume of about 70 mL. The concentrate was cooled to 0 to 10° C. and allowed to age. The solids were filtered, washed with 20 mL of a 4:1 ratio of n-heptane to ethyl acetate, and dried in a vacuum oven at 40° C. to provide 2a (9.9 g, 30.9 mmol). $^1$H NMR ($CDCl_3$, 400 MHz) δ 7.77-7.79 (m, 1H), 7.52-7.56 (m, 1H), 7.01-7.06 (m, 1H), 2.77 (d, J=3.2 Hz, 3H), 1.34 (s, 9H); MS (m/z): $[M+H]^+$ calcd for $C_{12}H_{16}BrFNOS$, 322.01; found, 321.94

Step B: Preparation of (R)-2-(5-bromo-2-fluorophenyl)-2-((R)-1,1-dimethylethylsulfinamido)-N-(4-methoxybenzyl)-N-(4-methylpropane-1-sulfonamide (4a)

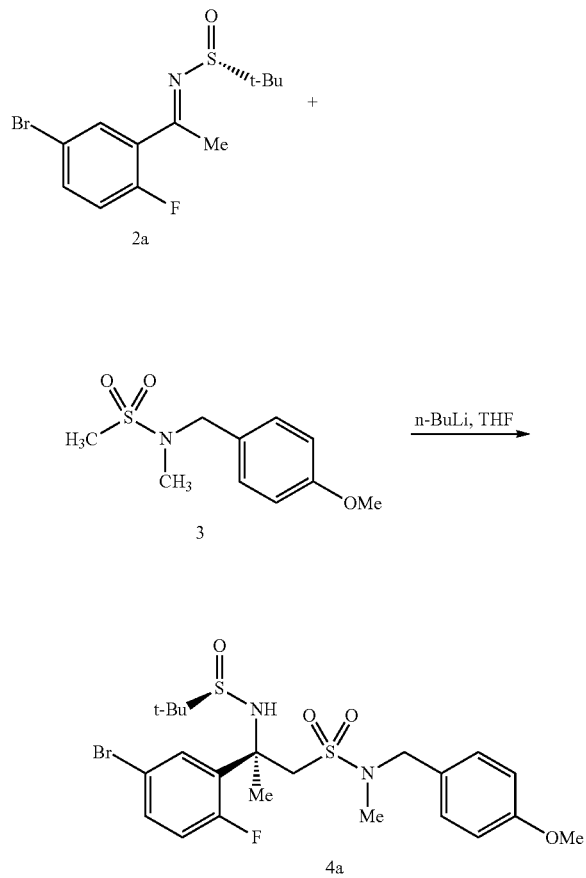

To a reactor (R-1) equipped with a temperature probe, nitrogen inlet, and agitator was charged N-(4-methoxybenzyl)-N-methylmethanesulfonamide 3 (71.6 g, 312 mmol) (Example 2) followed by THF (400 mL). Agitation was begun and the resulting solution was cooled to −15-20° C. n-BuLi (2.5 M in hexanes, 125 mL, 312 mmol) was then added at a sufficient rate to maintain the internal temperature. After 30 min, the reaction was cooled to −35-45° C.

To a second reactor (R-2) equipped with a temperature probe, nitrogen inlet, and agitator was charged (R,E)-N-(1-(5-bromo-2-fluorophenyl)ethylidene)-2-methylpropane-2-sulfinamide 2 (50 g, 156 mmol) followed by THF (100 mL). Agitation was begun and the resulting solution was added over 2 h to R-1. When the reaction in R-1 was deemed complete, it was quenched with water (500 mL) and warmed to ambient temperature. To the biphasic mixture was added 10% aqueous NaCl (250 mL) and the product was extracted twice with CH$_2$C$_2$(2×500 mL). The organic layers were combined, dried over MgSO$_4$, filter, and concentrated. The crude product was purified by silica gel chromatography to afford 4a (45.4 g, 82.4 mmol). $^1$H NMR (CDCl$_3$, 400 MHz) δ 7.68 (dd, J=1.9, 5.7 Hz, 1H), 7.41-7.45 (m, 1H), 7.20-7.24 (m, 2H), 6.99 (dd, J=6.9, 9.7 Hz, 1H), 6.84-6.89 (m, 2H), 5.89 (s, 1H), 4.19 (s, 2H), 3.82-3.92 (m, 2H), 3.80 (s, 3H), 2.71 (s, 3H), 1.92 (s, 3H), 1.37 (s, 9H); MS (m/z): [M+H]$^+$ calcd for C$_{22}$H$_{30}$BrFN$_2$O$_4$S$_2$, 551.09; found, 550.93.

Step C: Preparation of (R)-2-((R)-1,1-dimethylethylsulfinamido)-2-(2-fluoro-5-fluoropicolinamide)phenyl)-N-(4-methoxybenzyl)-N-methylpropane-1-sulfonamide (6a)

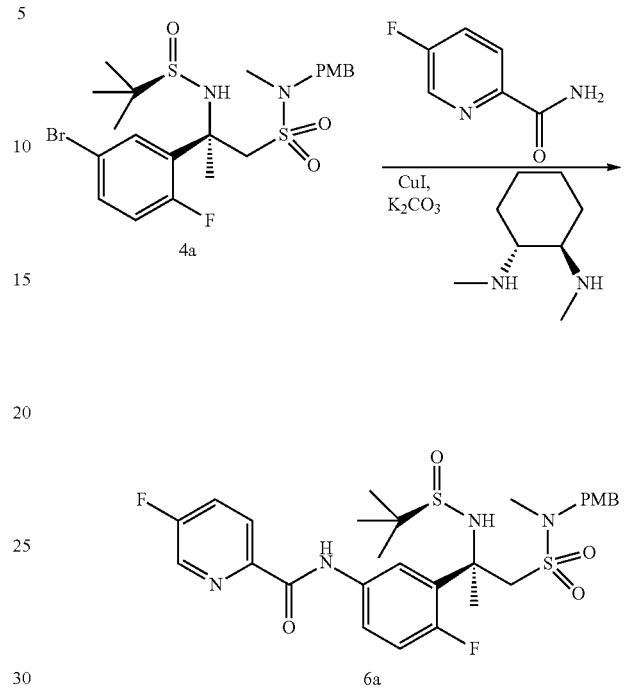

To a reactor (R-1) equipped with a temperature probe, nitrogen inlet and agitator was charged 5-fluoro-2-pyridinecarboxamide (1.049 g, 7.49 mmol), K$_2$CO$_3$ (2.82 g, 20.42 mmol), trans-N,N'-dimethylcyclohexane-1,2-diamine (2.147 mL, 13.61 mmol), copper(I) iodide (1.296 g, 6.81 mmol), toluene (8.5 mL) and 4a (37 wt % in toluene, 10 g, 6.81 mmol). Agitation was begun and the reaction was warmed to 80-90° C. When the reaction was deemed complete, the reaction was cooled to 20 to 30° C. In a separate reactor (R-2) equipped with an agitator was charged a 5% sodium chloride solution. The aqueous layer was separated and the organic layer was washed with 5% sodium chloride solution until the aqueous layer was clear. The organic layer was then concentrated to provide 6a (3.09 g, 5.08 mmol). $^1$H NMR (CDCl$_3$, 500 MHz) δ 10.79 (s, 1H), 8.74 (d, J=2.9 Hz, 1H), 8.24 (dd, J=4.2, 8.5 Hz, 2H), 7.98 (dt, J=2.8, 5.5 Hz, 1H), 7.92 (dq, J=2.4, 8.8 Hz, 1H), 7.17-7.23 (m, 2H), 6.90-6.95 (m, 2H), 5.58 (s, 1H), 4.00-4.10 (m, 2H), 3.81-3.90 (m, 2H), 3.74 (s, 3H), 2.56 (s, 3H), 1.94 (s, 3H), 1.20 (s, 9H); MS (m/z): [M+H]$^+$ calcd for C$_{28}$H$_{35}$F$_2$N$_4$O$_5$S$_2$, 609.20; found, 609.10.

Step D: Preparation of (R)-N-(3-(2-amino-1-(N-methylsulfamoyl)propan-2-yl)-4-fluorophenyl)-5-fluoropicolinamide (7)

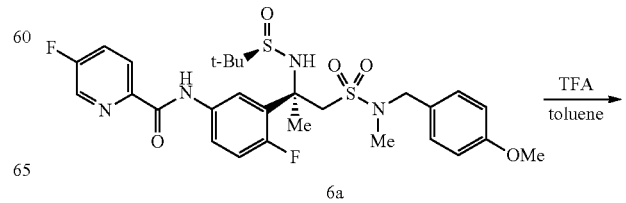

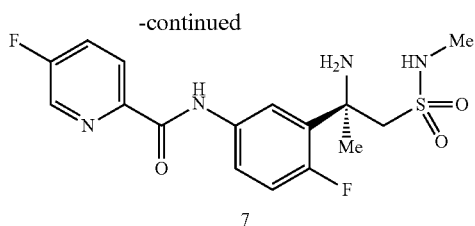

7

To a reactor (R-1) equipped with a temperature probe, nitrogen inlet, and agitator was charged (R)-2-((S)-1,1-dimethylethylsulfinamido)-2-(2-fluoro-5-fluoropicolinamide)phenyl)-N-(4-methoxybenzyl)-N-methylpropane-1-sulfonamide (6a) (24.1 g, 39.6 mmol) followed by toluene (121 mL). Agitation was begun, and then TFA (15.3 mL, 198 mmol) was charged. The resulting homogeneous solution was heated to 55-65° C. and agitated until the reaction was deemed complete. The reaction was cooled to ambient temperature and the product was extracted three times with water (3×100 mL). The combined aqueous layers were basified with 20% aqueous $Na_2CO_3$ to pH 10 and the product extracted three times with $CH_2Cl_2$ (3×300 mL). The combined organic layers were dried over $MgSO_4$, filtered, and concentrated to afford 7 (8.1 g, 21.1 mmol). $^1$H NMR (DMSO, 400 MHz) δ 10.57 (s, 1H), 8.73 (d, J=2.8 Hz, 1H), 8.24 (dd, J=4.8, 8.8 Hz, 1H), 8.15 (dd, J=2.5, 7.6 Hz, 1H), 7.98 (dt, J=2.8, 8.6 Hz, 1H), 7.85-7.90 (m, 1H), 7.11 (dd, J=8.7, 12.0 Hz, 1H), 6.81 (s, 1H), 3.63 (d, J=14.0 Hz, 1H), 3.45 (d, J=14.0 Hz, 1H), 2.50 (s, 3H), 1.53 (s, 3H); MS (m/z): [M+H]$^+$ calcd for $C_{16}H_{19}F_2N_4O_3S$, 385.11; found, 385.02.

Step E: Preparation of Verubecestat (I)

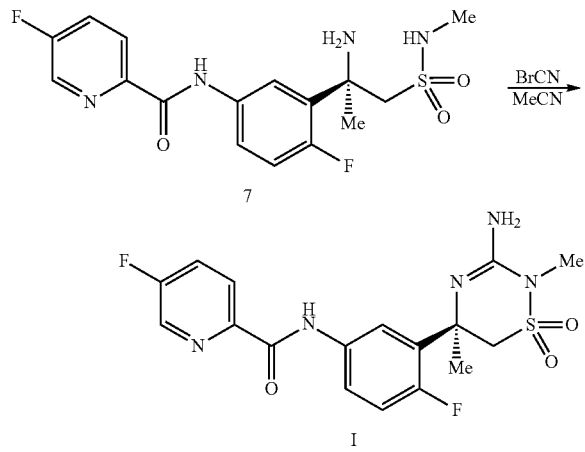

To a reactor (R-1) equipped with a temperature probe, nitrogen inlet, and agitator was charged (R)—N-(3-(2-amino-1-(N-methylsulfamoyl)propan-2-yl)-4-fluorophenyl)-5-fluoropicolinamide (7) (8.10 g, 21.1 mmol) followed by MeCN (40.5 mL). Agitation was begun and then BrCN (5 M in MeCN, 6.32 mL, 31.6 mmol) was charged. The slurry was heated to 80-90° C. and the resulting homogeneous solution was agitated until the reaction was deemed complete. The reaction was cooled to ambient temperature and diluted with EtOAc (122 mL). The organics were washed twice with saturated aqueous $NaHCO_3$ (2×80 mL), dried over $MgSO_4$, filtered, and concentrated. The solids were dissolved in EtOAc (52 mL) and heated to 40-50° C. Heptane (8.6 mL) was charged followed by a small amount of crystalline seeds of I. Additional heptane (69 mL) was added over 4 h and the slurry cooled to ambient temperature. The solids were collected, washed with heptane (26 mL), and dried under vacuum with a $N_2$ sweep to afford I (2.89 g, 7.06 mmol). $^1$H NMR (CDCl$_3$, 400 MHz) δ 9.69 (s, 1H), 8.20-8.32 (m, 2H), 7.99 (m, 1H), 7.52-7.66 (m, 2H), 7.07 (m, 1H), 5.33 (s, 2H), 3.97 (d, J=13.9 Hz, 1H), 3.67 (d, J=14.0 Hz, 1H), 3.22 (s, 3H), 1.79 (s, 3H); MS (m/z): [M+H]$^+$ calcd for $C_{17}H_{18}F_2N_5O_5S$, 410.11, found, 410.03.

Example 2

Preparation of N-(4-methoxybenzyl)-N-methylmethanesulfonamide

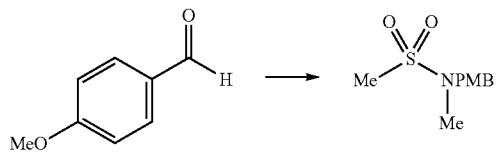

To a reactor (R1) equipped with a temperature probe, nitrogen inlet, and agitator was charged MeOH (92 kg) and 4-methoxybenzaldehyde (230.0 kg, 1689 mol). Agitation of R1 was begun and the internal temperature adjusted to 0° C. A solution of methylamine (30% in EtOH, 209.8 kg, 2026 mol) was charged to R1 dropwise over 6 h. The internal temperature of R1 was then adjusted to 20° C. and the mixture agitated until the condensation was judged to be complete, at which point the internal temperature was adjusted to 0° C. A second reactor (R2) was charged with THF (206 kg) followed by NaBH$_4$ (51.2 kg, 1351 mol). Agitation was begun and the reaction mixture from R1 was transferred to R2 over 8 h. The mixture was agitated until the reduction was judged to be complete. A third reactor (R3) was charged with water (115 kg) and 35% aqueous HCl (404 kg). Agitation of R3 was begun and the internal temperature was adjusted to 0° C. The reaction mixture from R2 was transferred to R3 over 12 h. The mixture was agitated until the reduction was judged to be complete. CH$_2$Cl$_2$ (969 kg) was charged to R3 followed by 50% aqueous NaOH (366 kg) over 6 h, at which point the internal temperature was adjusted to 20° C. The resulting solids were separated and washed with CH$_2$Cl$_2$ (157 kg) and the filtrate was transferred to R3. The layers were allowed to separate and the organic layer concentrated to approximately 1-2 volumes. CH$_2$Cl$_2$ (1220 kg) was charged to R3 and the contents concentrated; this process was repeated until the amount of residual water was judged to be satisfactory. Triethylamine (243 kg, 2400 mol) was charged to R3 and the contents of R3 transferred to a fourth reactor (R4). To R3 was charged methanesulfonyl chloride (223 kg, 1947 mol) and CH$_2$Cl$_2$ (635 kg), agitation was begun, and the internal temperature was adjusted to 0° C. The mixture in R4 was transferred to R3 dropwise over 12 h and then R3 was further agitated for 6 h. Water (572 kg) was then charged to R3 and the internal temperature adjusted to 20° C. The layers were allowed to separate and the organic layer washed twice with 2% aqueous NaCl (564 kg). The organic layer was concentrated under reduced pressure below 25° C. and then heptane (30 kg) was charged dropwise, followed by seed crystals (8 g) and additional heptane (1517 kg) over 20 h. The resulting slurry was agitated for 8 h before the solids were collected and washed with 10%

CH$_2$Cl$_2$ in heptane (320 kg) to provide N-(4-methoxybenzyl)-N-methylmethanesulfonamide (290.8 kg).

Example 3

Preparation of N-(3-acetyl-4-fluorophenyl)-5-fluoropicolinamide (5)

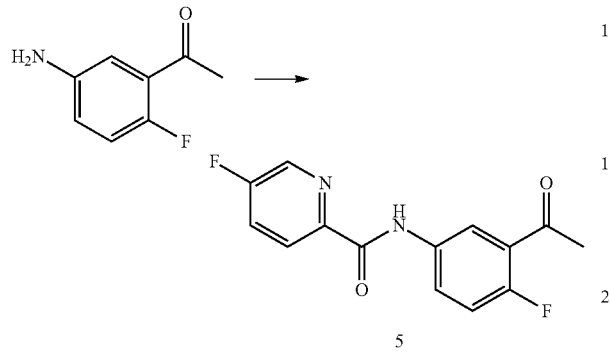

A round bottom flask equipped with an agitator was charged with 1-(5-amino-2-fluorophenyl)ethanone (1 g, 6.53 mmol), 5-fluoropicolinic acid (1.1 g, 7.80 mmol), THF (10 ml) and Hunig's Base (3.4 ml, 19.47 mmol). The reaction mixture was cooled to −10° C. and T$_3$P 50 wt % in 2-MeTHF (5.82 g, 9.14 mmol) was added slowly. The mixture is stirred at r.t. for 1 hour. Then the reaction mixture was cooled to 0° C. and water was added until a slurry was formed. The slurry was then filtered and rinsed with water to produce 1.80 g of N-(3-acetyl-4-fluorophenyl)-5-fluoropicolinamide.

Example 4

Example 4 describes one embodiment of the process illustrated in Scheme 2

Step A: Preparation of Amine (9a)

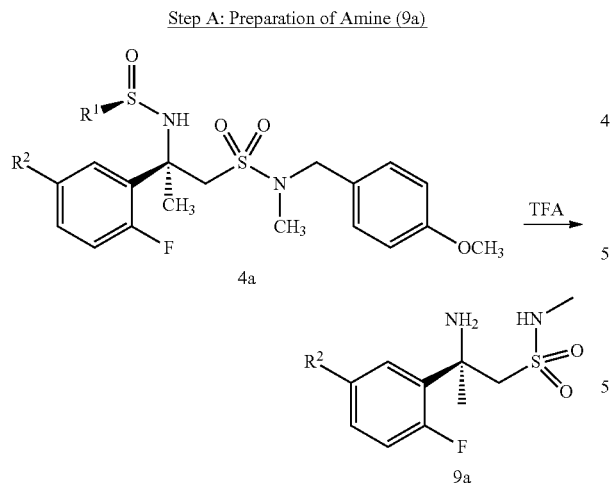

R$^1$ = tert-butyl
R$^2$ = Br

To a reactor (R1) equipped with a temperature probe, nitrogen inlet, and agitator was charged 4a (1 equiv). Toluene was charged to R1 and agitation was begun. Trifluoroacetic acid (10 equiv) was charged to R1 and the mixture heated to 60° C. until the reaction was judged complete. The contents were cooled to ambient temperature, at which point water was charged to R1. The layers were allowed to separate and the aqueous layer transferred to a second reactor (R2). The pH of the solution in R2 was adjusted to greater than 10 using a basic aqueous solution and the contents extracted three times with dichloromethane. The combined organic layers were dried over MgSO$_4$, filtered, and concentrated to afford 9a.

Step B: Preparation of Anime (7)

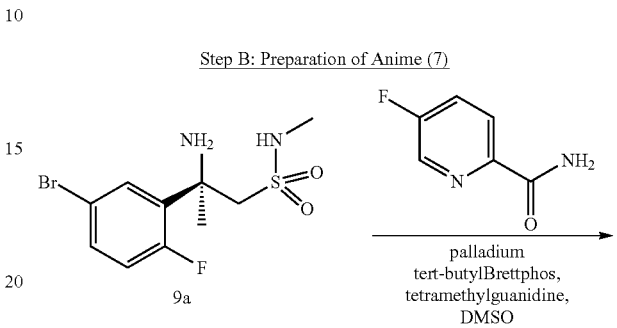

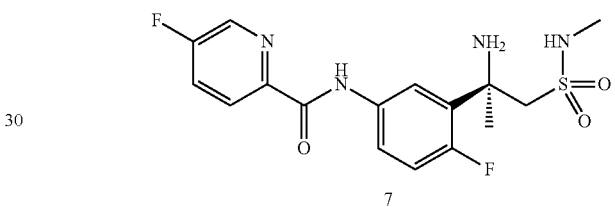

This description provided for this step is prophetic.

To reactor (R1) equipped with a temperature probe, nitrogen inlet, and agitator is charged 9a (1 equiv), 2-fluoropicolinamide (1.1 equiv), and palladium tert-butyl-BrettPhos G3 precatalyst (0.03 equiv). Dimethylsulfoxide and 1,1,3,3-tetramethylguanidine (3 equiv) are charged to R1 and agitation is begun. The mixture is heated to 70° C. until the reaction is judged complete. The contents are cooled to ambient temperature, at which point ethyl acetate is charged and the mixture is washed three times with water. The organic layer is dried over MgSO$_4$, filtered, and concentrated to afford 7.

Example 5

Example 5 describes one embodiment of the process illustrated in Scheme 3

Step A: Preparation of Amine (8a)
(wherein R$^1$ is tert-butyl) from Ketone (5)

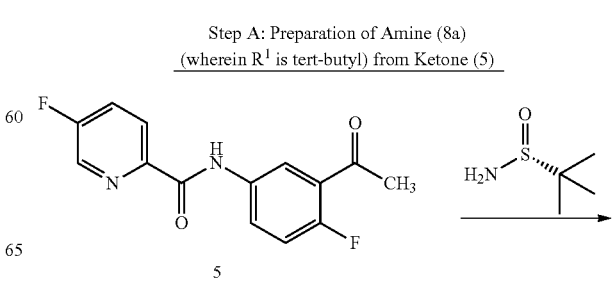

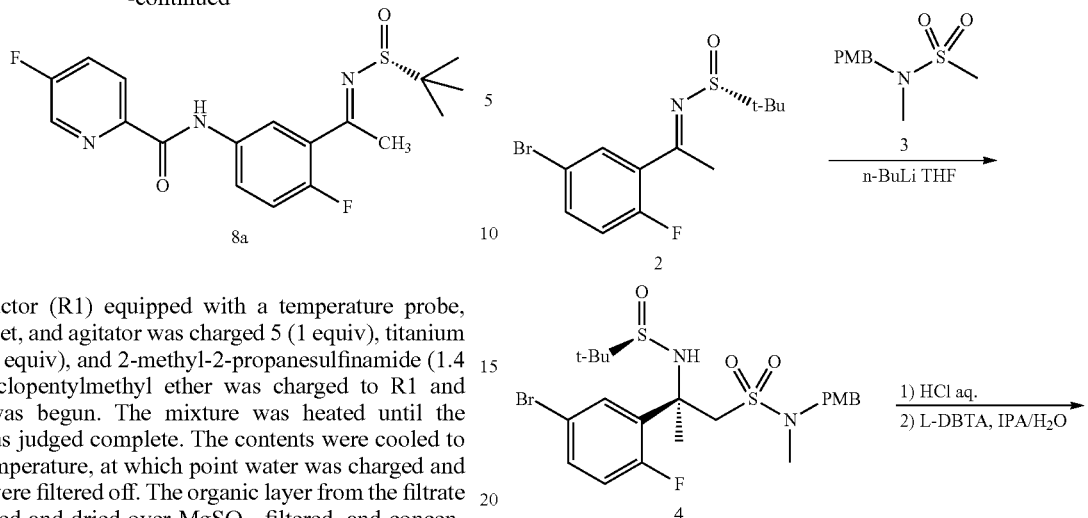

To a reactor (R1) equipped with a temperature probe, nitrogen inlet, and agitator was charged 5 (1 equiv), titanium ethoxide (2 equiv), and 2-methyl-2-propanesulfinamide (1.4 equiv). Cyclopentylmethyl ether was charged to R1 and agitation was begun. The mixture was heated until the reaction was judged complete. The contents were cooled to ambient temperature, at which point water was charged and the solids were filtered off. The organic layer from the filtrate was collected and dried over MgSO₄, filtered, and concentrated to afford 8a.

Step B: Preparation of PMB-Protected Sulfonamide (6)

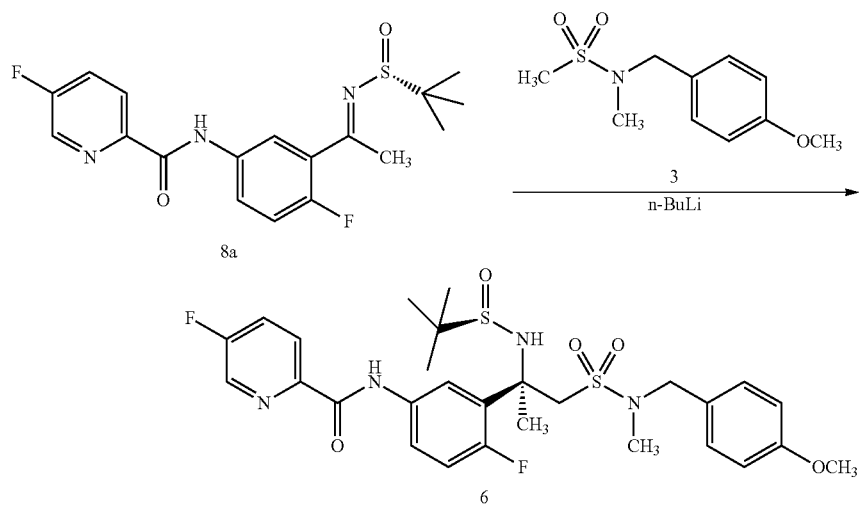

To a reactor (R1) equipped with a temperature probe, nitrogen inlet, and agitator was charged 3 (1.75 equiv) followed by THF. Agitation was begun and the resulting solution was cooled to −15-20° C. n-BuLi (2.5 M in hexanes, 1.75 equiv) was then added at a sufficient rate to maintain the internal temperature. After 30 min, the reaction was cooled to −35-45° C. To a second reactor (R2) equipped with a temperature probe, nitrogen inlet, and agitator was charged 8a (1.00 equiv). Agitation was begun and the resulting solution was added over 2 h to R1. When the reaction in R1 was deemed complete, it was quenched with water and warmed to ambient temperature. To the biphasic mixture was added 10% aqueous NaCl and the product was extracted twice with CH₂Cl₂. The organic layers were combined, dried over MgSO₄, filter, and concentrated. The crude product was purified by silica gel chromatography to afford 6.

Example 6

Example 6 describes one embodiment of the process illustrated in Scheme 5

-continued

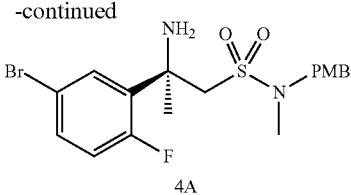

To a reactor (R1) equipped with a temperature probe, nitrogen inlet, and agitator was charged 3 (272 g, 1.36x) followed by THF. The temperature of R1 was adjusted to −20 to −15° C. nBuLi (2.27M, 1.5 to 1.6x) was added dropwise to R1 over 2h at a rate to maintain the internal temperature of the reaction at −20 to −15° C. The batch was then agitated at −20 to −15° C. for 0.5 to 1 h. The temperature of R1 was adjusted to −70 to −60° C. To a reactor (R2) equipped with a temperature probe, nitrogen inlet, and agitator was charged 2 (200 g, 1x) followed by THF. The batch in R2 was agitated for 0.5h at 25-30° C. Add the reaction mixture in R2 into R1 at −70 to −60° C. over 2 h. The resulting reaction mixture in R1 was stirred at −70° C. to −60° C. for 0.5 to 1 h. When the reaction in R1 was deemed complete, the reaction mixture was quenched by adding a solution of AcOH (75 g, 0.37-0.40×) in THF (18 g, 0.05-0.1×) to R1 at −70° C. to −60° C. in 1 h. The temperature of R1 was adjusted to 15 to 25° C. 232.4 g of 4 was obtained by assay. 500 g of 6N HCl aqueous solution was charged to R1 and agitated at 15-25° C. for 1 to 2 h. When the reaction was deemed complete, ethyl acetate (640 g, 3-3.5×) and 600 g (3-3.5×) pure water was charged into R1. The aqueous layer was separated and removed. 10% aqueous $K_2CO_3$ solution (1.4 kg, 6.5 to 7.5×) was charged to R1 within 0.5 h (pH of aqueous layer was 6 to 7). The organic layer was washed with pure water (700 g, 3-4×) and the aqueous layer was removed. The organic phase was concentrated under vacuum at 40° C. to 50° C., co-distilling with 2-propanol under vacuum at 40 to 50° C. until the residual THF and ethyl acetate in the resulting solution (3.0 to 4.0×) was ≤0.05% (2.3 kg of 2-propanol was used in the azeotropic removal of THF and ethyl acetate). Additional 2-propanol was charged to R1 (540 g (2.0 to 4.0×) followed by dibenzoyl-L-tartaric acid (90.7 g, 0.45-0.50×). Pure water was then charged to R1 (820 g, 4.0-4.5×) and R1 was warmed to 65° C. for 0.5 h. The batch was cooled to 50° C. and seeded. The batch in R1 was further cooled to 5 to 15° C. over 4h and aged for 10-20 h. The batch was filtered and the wet cake was slurried with 400 g (1.5-2.5×) 2-propanol/water (v/v 3:2). The wet cake was washed with pure water twice (600 g, 3.0-4.0×). The wet cake was transferred to R1 followed by toluene (870 g, 4.3 to 4.5×). 30% $K_2CO_3$ aqueous solution (1 kg, 5.0 to 6.0×) was charged to R1 and the batch was stirred for 0.5 h at 20 to 30° C. The aqueous layer was separated and 4A was carried forward as a toluene solution.

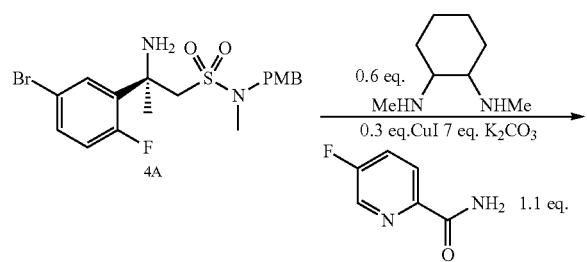

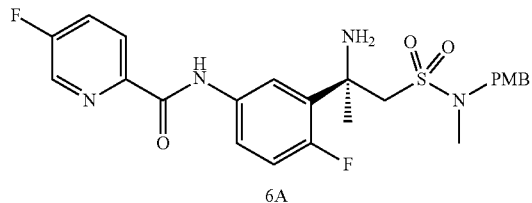

To a reactor (R1) equipped with a temperature probe, nitrogen inlet and agitator was charged 5-fluoropicolinamide (11.93 g), $K_2CO_3$ (74.9 g), trans-N,N'-dimethylcyclohexane-1,2-diamine (6.6 g), copper(I) iodide (4.42 g), toluene (150 g) and 4a (34 wt % in toluene, 34.5 g). The mixture was sparged with argon for 2h to remove oxygen. Agitation was begun and the reaction was warmed to 80-90° C. The reaction was quenched by adding 13.9 g ethane-1,2-diamine and stirred for 0.5 h. The organic layer was washed with AcOH (27.86 g) and water (172 g) followed by 7% $NaHCO_3$ solution. The organic layer was then concentrated to provide 6A. $^1$H NMR (CDCl$_3$, 400 MHz) δ 9.97 (s, 1H), 8.55 (d, 2H), 8.42 (dd, 1 h), 8.01 (m, 2H), 7.65 (m, 1H), 7.29 (m, 3H), 7.23 (m, 6H), 6.93 (d, 2H), 4.21 (m, 1H), 3.97 (m, 1H), 3.89 (s, 3H), 3.48 (d, 1H), 2.66 (s, 3H), 1.77 (s, 3H).

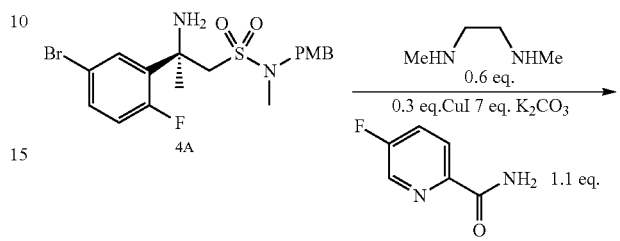

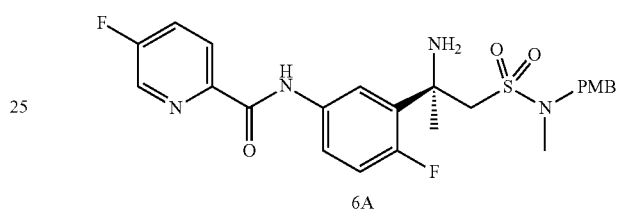

The following describes an alternate procedure for the synthesis of 6A from 4A using or N,N'-dimethylethylenediamine (DMEDA). To an autoclave reactor (R1) equipped with mechanical stirror, temperature probe, 4A solution in toluene (178.66 g×19.6%=35 g 4A), 5-fluoropicolinamide (12.1 g) and $K_2CO_3$ aqueous solution (76 g $K_2CO_3$, in 105 g water), were charged, followed by 4.16 g DMEDA. The mixture was sparged with argon for 2 h to remove oxygen. Then, 4.49 g CuI was charged and the mixture was sparged with argon for 1 hour. The autoclave was then sealed and heated to 105° C. (internal temperature) for 24 h with agitation. The reaction was quenched by adding 14.15 g ethane-1.2-diamine and stirred for 0.5 h. The organic layer was washed with AcOH (28.3 g) in water (172 g) followed by 7% $NaHCO_3$ solution. The organic layer was then concentrated to provide 6A.

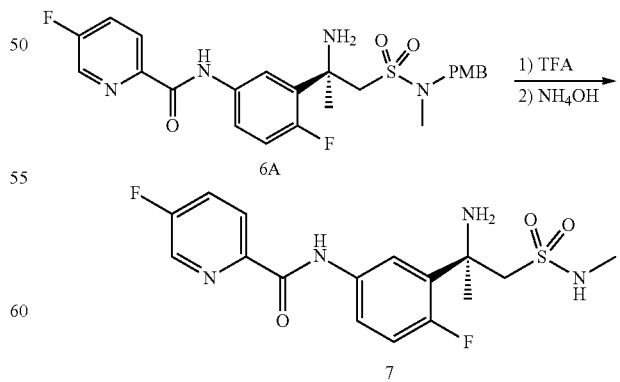

To a reactor (R1) equipped with a temperature probe, nitrogen inlet and agitator was charged 6A (49.9 g) and trifluoroacetic acid (271 g, 5.4×). The mixture was stirred at 55 to 65° C. for 3 h. The temperature of the batch was adjusted to 15 to 25° C. and stirred for 1 to 2 h. Glycolic acid (80 g) and water (320 g) were charged to R2 and the mixture was stirred at 15 to 25° C. until the mixture became clear biphasic solution. The batch in R2 was charged into R1 and stirred at 15 to 25° C. for 1 to 2 h. The layers in R1 were then separated. The aqueous layer of R1 was added dropwise to a reactor (R3) containing NH$_4$OH (450 g) at 20 to 30° C. over 6 to 8 h. The mixture was then stirred at 15 to 25° C. for 15 to 20 h, filtered and the wet cake washed with water three times, then dried under reduced pressure at 40 to 50° C. for 30 to 40 h to obtain 7. $^1$H NMR (DMSO, 400 MHz) δ 10.57 (s, 1H), 8.73 (d, J=2.8 Hz, 1H), 8.24 (dd, J=4.8, 8.8 Hz, 1H), 8.15 (dd, J=2.5, 7.6 Hz, 1H), 7.98 (dt, J=2.8, 8.6 Hz, 1H), 7.85-7.90 (m, 1H), 7.11 (dd, J=8.7, 12.0 Hz, 1H), 6.81 (s, 1H), 3.63 (d, J=14.0 Hz, 1H), 3.45 (d, J=14.0 Hz, 1H), 2.50 (s, 3H), 1.53 (s, 3H); MS (m/z): [M+H]$^+$ calcd for C$_{16}$H$_{19}$F$_2$N$_4$O$_3$S, 385.11; found, 385.02.

What is claimed is:

1. A process for the preparation of a compound of Formula (I):

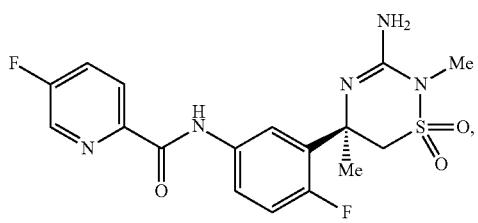

comprising:
combining an amine

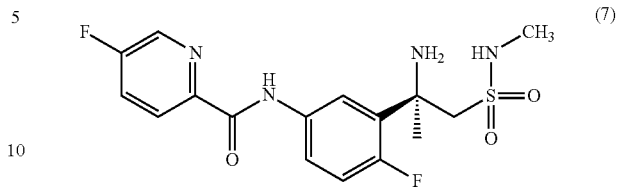

with a weak base;
then reacting said mixture with a cyanating agent followed by treatment with a Brønsted base to form the compound of Formula (I).

2. The process of claim 1, wherein the weak base is sodium bicarbonate or potassium phosphate dibasic.

3. The process of claim 2, wherein the weak base is sodium bicarbonate.

4. The process of claim 3, wherein amine (7) is dissolved in a solvent prior to the addition of the weak base.

5. The process of claim 4, wherein the solvent is a mixture of an organic solvent and water.

6. The process of claim 5, wherein the cyanating agent is selected from the group consisting of cyanogen, cyanogen bromide, cyanogen fluoride, cyanogen chloride, cyanogen iodide, 2-methoxyphenyl cyanate, 4-methoxyphenyl cyanate, 4-phenylphenyl cyanate, and bisphenol A cyanate.

7. The process of claim 6, wherein the cyanating agent is cyanogen bromide.

8. The process of claim 7, wherein the reaction temperature is from 45 to 50° C.

9. The process of claim 8, wherein the Bronsted base is sodium hydroxide.

* * * * *